(12) United States Patent
Wonsey et al.

(10) Patent No.: US 7,655,402 B2
(45) Date of Patent: Feb. 2, 2010

(54) DIAGNOSES AND THERAPEUTICS FOR CANCER

(75) Inventors: Diane R. Wonsey, Concord, MA (US); Maximillian T. Follettie, Belmont, MA (US)

(73) Assignee: Wyeth LLC, Madison, NJ (US)

( * ) Notice: Subject to any disclaimer, the term of this patent is extended or adjusted under 35 U.S.C. 154(b) by 283 days.

(21) Appl. No.: 11/051,679

(22) Filed: Feb. 4, 2005

(65) Prior Publication Data

US 2006/0014686 A1    Jan. 19, 2006

Related U.S. Application Data

(60) Provisional application No. 60/606,378, filed on Sep. 1, 2004, provisional application No. 60/557,130, filed on Mar. 26, 2004, provisional application No. 60/542,758, filed on Feb. 6, 2004.

(51) Int. Cl.
C12Q 1/68    (2006.01)
(52) U.S. Cl. .............................. 435/6; 436/64; 536/23.5; 530/350
(58) Field of Classification Search ................ 435/7.23, 435/6; 530/350; 436/64; 536/23.5
See application file for complete search history.

(56) References Cited

FOREIGN PATENT DOCUMENTS

| WO | WO-99/32619 | 7/1999 |
|---|---|---|
| WO | WO-00/44895 | 8/2000 |
| WO | WO-00/63364 | 10/2000 |
| WO | WO-01/75164 | 10/2001 |
| WO | WO-01/92513 | 12/2001 |
| WO | WO-02/061134 | 8/2002 |
| WO | WO-02/092013 | 11/2002 |

OTHER PUBLICATIONS

Kim et al. (J. Biol. Chem. Jun 10, 2005; 280 (23): 22278-22286).*
Yoshida et al. (Gastroenterol. 2007; 132: 1420-1431).*
De Plaen et al. (Immunogenetics. 1994; 40: 360-369).*
Ward (Developmental Oncology 1985; 21: 91-106).*
Rae et al. (International Journal of Cancer. 2000; 88: 726-732).*
Tockman et at (Cancer Research 1992; 52: 2711s-2718s).*
Chen et al. (Mol. Cell. Proteomics. Apr. 2002; 1 (4): 304-313).*
Liu et al. (Cancer J. Sep.-Oct. 2001; 7 (5): 395-403).*
Lichtinghagen et al. (Eur. Urol. 2002; 42 (4): 398-406).*
Roessler et al. (Mol. Cell. Prot. 2006; 5 (11): 2092-2101).*
Zolg et al. (Mol. Cell. Prot. 2004; 3 (4): 345-354).*
Altieri, "Validating Survivin as a Cancer Therapeutic Target" Nat. Rev. Cancer 3: 46-54 (2003).
Ausubel et al., "Hybridization Analysis of DNA Blots" Current Protocols in Molecular Biology, §§ 2.10, 6.3-6.4, John Wiley & Sons, Inc. (1995).
Brown et al., "ATR Disruption Leads to Chromosomal Fragmentation and Early Embryonic Lethality" Genes and Development, 14: 397-402 (2000).
Brummelkamp et al., "A System for Stable Expression of Short Interfering RNAs in Mammalian Cells" Science, 296: 550-553 (2002).
Chan et al., "14-3-3Sigma is Required to Prevent Mitotic Catastrophe After DNA Damage" Nature, 401: 616-620 (1999).
DeLuca et al., "hNuf2 Inhibition Blocks Stable Kinetochore-Microtubule Attachment and Induces Mitotic Cell Death in HeLa Cells" Journal of Cell Biology, 159(4): 549-555 (2002).
Dimri et al., "A Biomarker That Identifies Senescent Human Cells in Culture and in Aging Skin in Vivo" Proc Natl Acad Sci USA, 92:9363-9367 (1995).
Dutertre et al., "Phosphorylation of CDC25B by Aurora-A at the Centrosome Contributes to the G2-M Transition" Journal of Cell Science, 117: 2523-2531 (2004).
Elbashir et al., "Duplexes of 21-Nucleotide RNAs Mediate RNA Interference in Cultured Mammalian Cells" Nature, 411:494-498 (2001).
Elbashir et al., "RNA Interference is Mediated by 21- and 22-Nucleotide RNAs" Genes and Development, 15:188-200 (2001).
Faragher et al., "Nek2A Kinase Stimulates Centrosome Disjunction and is Required for Formation of Bipolar Mitotic Spindles" Molecular Biology of the Cell, 14:2876-2889 (2003).
Fontijn at al., "The Human Kinesin-Like Protein RB6K is Under Tight Cell Cycle Control and is Essential for Cytokinesis" Molecular and Cellular Biology, 21(8): 2944-2955 (2001).
Fry at al., "A Centrosomal Function for the Human Nek2 Protein Kinase, a Member of the NIMA Family of Cell Cycle Regulators" EMBO Journal 17(2): 470-481 (1998).
Goshima et al., "Human Centromere Chromatin Protein hMisI2, Essential for Equal Segregation, is Independent of CENP-A Loading Pathway" Journal of Cell Biology 160(1): 25-39 (2003).
Grossman et al., "Inhibition of Melanoma Tumor Growth in Vivo by Survivin Targeting" Proc Natl Acad Sci USA 98(2): 635-640 (2001).
Gyuris et al., "Cdi1, a Human G1 and S Phase Protein Phosphatase that Associates with Cdk2" Cell, 75:791-803 (1993).
Hill et al., "Evaluation of Normalization Procedures for Oligonucleotide Array Data Based on Spiked cRNA Controls" Genome Biology, 2(12): RESEARCH0055.1-0055.13 (2001).
Hinchcliffe et al., "Requirement of a Centrosomal Activity for Cell Cycle Progression Through G1 into S phase" Science, 291:1547-1550 (2001).
Hinchcliffe et al., "It takes two to tango"; understanding how centrosome duplication is regulated throughout the cell cycle, Genes and Development, 15: 1167-1181 (2001).
Howman et al., "Early disruption of centromeric chromatin organization in centromere protein A (Cenpa) null mice" Proc Natl Acad Sci USA, 97(3):1148-1153 (2000).
Kalinichenko at al., "Differential expression of forkhead box transcription factors following butylated hydroxytoluene lung injury" Am. J. Physiol. Lung Cell Mol. Physiol., 280:L695-L704 (2001).

(Continued)

*Primary Examiner*—Stephen L Rawlings
(74) *Attorney, Agent, or Firm*—Joseph E. Zahner

(57) ABSTRACT

Methods and compositions for treating and diagnosing cancer and screening for agents for such treatment and diagnosis are provided. The methods involve screening for agents that modulate the activity or expression of FOXM1, which has been discovered herein to play a role in cell growth and cell cycle regulation. Methods for treating cancer, methods for modulating the activity or expression of FOXM1, methods for diagnosing a subject that has or is at risk of developing cancer, and pharmaceutical compositions are also provided.

6 Claims, 10 Drawing Sheets

OTHER PUBLICATIONS

Kalinichenko et al., "Foxm1b transcription factor is essential for development of hepatocellular carcinomas and is negatively regulated by the p19ARF tumor suppressor", Genes and Development, 18:830-850 (2004).

Kawasaki at al., "Inhibition of apoptosis by survivin predicts shorter survival rates in colorectal cancer", Cancer Research, 58:5071-5074 (1998).

Khodjakov et al., "Centrosomes enhance the fidelity of cytokinesis in vertebrates and are required for cell cycle progression", Journal of Cell Biology, 153(1): 237-242 (2001).

Korver at al., "The winged-helix transcription factor Trident is expressed in cycling cells" Nucleic Acids Research, 25(9): 1715-1719 (1997).

Korver et al., "Uncoupling of S phase and mitosis in cardiomyocytes and hepatocytes lacking the winged-helix transcription factor Trident", Current Biology Ltd., 8:1327-1330 (1998).

Lai et al., "RBP1 induces growth arrest by repression of E2F-dependent transcription" ncogene 18: 2091-2100 (1999).

Lee et al., "Overexpression of kinase-associated phosphatase (KAP) in breast and prostate cancer and inhibition of the transformed phenotype by antisense KAP expression", Molecular and Cellular Biology, 20(5): 1723-1732 (2000).

Leung et al., "Over-expression of FoxM1 stimulates cyclin B1 expression", FEBS Letters, 507:59-66 (2001).

Li et al., "Pleiotropic cell-division defects and apoptosis induced by interference with survivin function", Nature Cell Biology, 1: 461-466 (1999).

Liang et al., "Mitotic cell death in BEL-7402 cells induced by enediyne antibiotic lidamycin is associated with centrosome overduplication", World J Gastroenterol, 10(18): 2632-2636 (2004).

Lingle et al., "Centrosome amplification drives chromosomal instability in breast tumor development" Proc Natl Acad Sci USA, 99(4): 1978-1983 (2002).

Lockhart et al., "Expression monitoring by hybridization to high-density oligonucleotide arrays", Nature Biotechnology, 14: 1675-1680 (1996).

Margottin-Goguet et al., "Prophase destruction of Emi1 by the SCF(betaTrCP/Slimb) ubiquitin ligase activates the anaphase promoting complex to allow progression beyond prometaphase", Developmental Cell 4: 813-826 (2003).

Meraldi et al., "Aurora-A overexpression reveals tetraploidization as a major route to centrosome amplification in p53-/- cells", EMBO Journal, 21(4): 483-492 (2002).

Meraldi et al., "Centrosome duplication in mammalian somatic cells requires E2F and Cdk2-cyclin A" Nature Cell Biology, 1: 88-93 (1999).

Monzo et al., "A novel anti-apoptosis gene: Re-expression of survivin messenger RNA as a prognosis marker in non-small-cell lung cancers", Journal of Clinical Oncology, 17(7): 2100-2104 (1999).

Nakayama et al., "Targeted disruption of Skp2 results in accumulation of cyclin E and p27(Kip1), polyploidy and centrosome overduplication", EMBO Journal, 19(9): 2069-2081(2000).

Nitta et al., "Spindle checkpoint function is required for mitotic catastrophe induced by DNA-damaging agents", Oncogene, 23: 6548-6558 (2004).

O'Connor et al., "Regulation of apoptosis at cell division by p34cdc2 phosphorylation of survivin", Proc Natl Acad Sci USA 97(24): 13103-13107 (2000).

Okabe et al., "Genome-wide analysis of gene expression in human hepatocellular carcinomas using cDNA microarray: identification of genes involved in viral carcinogenesis and tumor progression", Cancer Research, 61: 2129-2137 (2001).

Pihan et al., "Centrosome defects and genetic instability in malignant tumors" Cancer Research, 58: 3974-3985 (1998).

Saavedra et al., "Inactivation of E2F3 results in centrosome amplification", Cancer Cell, 3: 333-346 (2003).

Sambrook et al., "Molecular Cloning: A Laboratory Manual", Chs. 9 & 11, Cold Spring Harbor Laboratory Press, Cold Spring Harbor, NY (1989).

Strausfeld et al., "Both cyclin A and cyclin E have S-phase promoting (SPF) activity in Xenopus egg extract", Journal of Cell Science, 109: 1555-1563 (1996).

Takai et al., "Aberrant cell cycle checkpoint function and early embryonic death in Chk1(-/-) mice", Genes and Development, 14: 1439-1447 (2000).

Tanaka et al., "Expression of survivin and its relationship to loss of apoptosis in breast carcinomas", Clinical Cancer Research, 6: 127-134 (2000).

Teh et al., "FOXM1 is a downstream target of Gli1 in basal cell carcinomas", Cancer Research, 62: 4773-4780 (2002).

Tomonaga et al., "Overexpression and mistargeting of centromere protein-A in human primary colorectal cancer", Cancer Research, 63: 3511-3516 (2003).

Uren et al., "Survivin and the inner centromere protein INCENP show similar cell-cycle localization and gene knockout phenotype", Current Biology, 10: 1319-1328 (2000).

Wang et al., "Earlier expression of the transcription factor HFH-11B diminishes induction of p21 (CIP1/WAF1) levels and accelerates mouse hepatocyte entry into S-phase following carbon tetrachloride liver injury", Hepatology, 33(6): 1404-1414 (2001).

Wang et al., "Rapid hepatocyte nuclear translocation of the Forkhead Box M1B (FoxM1B) transcription factor caused a transient increase in size of regenerating transgenic hepatocytes" Gene Expression, 11: 149-162 (2003).

Wang et al., "The Forkhead Box m1b transcription factor is essential for hepatocyte DNA replication and mitosis during mouse liver regeneration", Proc Natl Acad Sci USA, 99(26): 16881-16886 (2002).

Wang et al., "Increased levels of forkhead box M1B transcription factor in transgenic mouse hepatocytes prevent age-related proliferation defects in regenerating liver", Proc Natl Aced Sci USA 98(20): 11468-11473 (2001).

Westendorf et al., "Cloning of cDNAs for M-phase phosphoproteins recognized by the MPM2 monoclonal antibody and determination of the phosphorylated epitope", Proc Natl Acad Sci USA, 91: 714-718 (1994).

Wiese et al., "Gamma-tubulin complexes and their interaction with microtubule-organizing centers", Current Opinion in Structural Biology, 9: 250-259 (1999).

Yao et al., "Molecular analysis of a novel winged helix protein, WIN. Expression pattern, DNA binding property, and alternative splicing within the DNA binding domain", Journal of Biological Chemistry, 272(32): 19827-19836 (1997).

Ye et al., "Premature expression of the winged helix transcription factor HFH-11B in regenerating mouse liver accelerates hepatocyte entry into S phase", Molecular Cellular Biology, 19(12): 8570-8580 (1999).

Ye et al., "Hepatocyte nuclear factor 3/fork head homolog 11 is expressed in proliferating epithelial and mesenchymal cells of embryonic and adult tissues", Molecular and Cellular Biology, 17(3): 1626-1641 (1997).

Zhou et al. "The DNA damage response: putting checkpoints in perspective", Nature, 408: 433-439 (2000).

Singer, Maxine et al. *Genes and Genomes*. Chapter 3. 1991. ISBN: 0-935702-17-2. pp. 133-134.

Wang, Zhiwie et al. "Down-regulation of Forkhead Box M1 Transcription Factor Leads to the Inhibition of Invasion and Angiogenesis of Pancreatic Cancer Cells." *Cancer Research*. Sep. 1, 2007. 67: (17). pp. 8293-8300.

Pilarsky, et al., "Identification and Validation of Commonly Overexpressed Genes in Solid Tumors by Comparison of Microarray Data", Neoplasia, 6(6):744-750 (2004).

\* cited by examiner

A transfect → select days 2-8 → cell growth days 9-15 → day 21

Western timelapse microscopy
immunofluorescence

BrdU assay
SA-β-gal staining

B

C negative control

FOXM1 shRNA scalebar=20μM

| probe set | Gene Symbol | GO molecular function | Fold change | Fold Change p-value |
|---|---|---|---|---|
| | | Transcription | | |
| 202580_x_at | FOXM1 | RNA polymerase II transcription factor | -5.69 | 4.11E-06 |
| 209187_at | DR1 | DNA binding, transcription co-repressor | -3.92 | 1.41E-04 |
| 218490_s_at | ZNF302 | DNA binding | -2.08 | 3.06E-03 |
| 209786_at | HMGN4 | DNA binding | -1.80 | 2.01E-03 |
| 203536_s_at | CIAO1 | transcriptional regulation | -1.85 | 1.69E-03 |
| 205062_x_at | RBBP1 | chromatin binding, transcription factor | 1.70 | 5.28E-03 |
| 204080_at | TOE1 | transcriptional repressor activity | -1.71 | 4.68E-05 |
| | | Cell cycle and chromosome segregation | | |
| 209714_s_at | CDKN3 | protein tyrosine/serine/threonine phosphatase | -2.10 | 1.66E-06 |
| 201853_s_at | CDC25B | protein tyrosine phosphatase | -1.96 | 1.64E-04 |
| 218755_at | KIF20A | ATP binding, motor, protein transporter | -1.78 | 6.22E-04 |
| 211080_s_at | NEK2 | kinase, cytokinesis, centrosome | -1.78 | 1.10E-03 |
| 203418_at | CCNA2 | cyclin-dependent protein kinase | -1.77 | 4.67E-04 |
| 210821_x_at | CENPA | chromatin binding | -1.72 | 1.02E-03 |
| | | Metabolism | | |
| 205749_at | CYP1A1 | cytochrome P450, oxidoreductase | -1.77 | 4.72E-03 |
| 202382_s_at | GNPI | glucosamine-6-phosphate deaminase | -1.93 | 6.35E-03 |
| 217989_at | RETSDR2 | oxidoreductase | -1.71 | 4.95E-04 |
| | | Cytokine | | |
| 205767_at | EREG | epidermal growth factor receptor ligand | 1.73 | 3.09E-04 |
| 202859_x_at | IL8 | chemokine, interleukin-8 receptor ligand | 1.84 | 9.33E-03 |
| | | Other | | |
| 212702_s_at | BICD2 | microtubule dynamics | -1.74 | 6.06E-04 |
| 213478_at | KIAA1026 | unknown | -1.73 | 8.85E-03 |
| 209885_at | ARHD | GTP binding, Rho small monomeric GTPase | -2.64 | 5.69E-04 |
| 203890_s_at | DAPK3 | kinase, induction of apoptosis | -1.76 | 2.50E-05 |
| 204944_at | PTPRG | tyrosine phosphatase | -2.06 | 1.45E-03 |
| 203414_at | MMD | macrophage maturation-associated | -1.88 | 2.00E-03 |
| 200699_at | RPL23 | structural constituent of ribosome | -1.75 | 1.20E-03 |
| 219770_at | FLJ11753 | glycosyltransferase-like | -2.58 | 2.25E-06 |
| 202627_s_at | SERPINE1 | plasminogen activator, serpin | -1.72 | 7.55E-04 |

FIG. 10

DIAGNOSES AND THERAPEUTICS FOR CANCER

CLAIM OF PRIORITIES

This application claims priorities from provisional applications 60/606,378 (filed on Sep. 1, 2004), 60/557,130 (filed on Mar. 26, 2004), and 60/542,758 (filed on Feb. 6, 2004).

FIELD OF THE INVENTION

This invention relates to the fields of diagnoses and therapeutics for cancer, including, but not limited to, methods of screening for cancer, methods of screening for agents to treat cancer, and methods for treating cancer.

BACKGROUND OF THE INVENTION

The present invention relates generally to diagnoses and therapeutics for cancer. Generally, the invention relates to methods of screening for cancer, methods of screening for agents to treat cancer and methods for treating cancer.

The cell cycle is a highly regulated event with each cycle comprising G1 phase for cell preparation before DNA replication, S phase for DNA replication, G2 phase for cell growth and preparation for division, and M phase for mitosis (nuclear division) and cytokinesis (cell division) to complete the cycle. In a normal cell, the S-M phases, separated by the preparative G1 and G2 phases, are tightly coupled so that only one round of S phase precedes each mitosis and mitosis is not initiated until one round of DNA replication is completed. As a result, chromosomal DNA is replicated precisely once per cell cycle. Failure of this S-M coupling results in aneuploidy (gain or loss of DNA) leading to abnormality in cell growth and function.

Centrosomes are the primary components of the microtubule organizing center in mammalian cells. The regulation of centrosome duplication in mammalian cells is tightly controlled in order to maintain genomic integrity and prevent aneuploidy. Hinchcliffe and Sluder, *Gene Dev.* 15:1167-1181 (2001). In addition to directing formation of the mitotic spindle, recent evidence indicates that the centrosome participates in cell cycle regulation. Hinchcliffe et al., *Science* 291: 1547-1550 (2001); Khodjakov and Rieder, *J. Cell Biol.* 153: 237-242 (2001). Cancer cells frequently contain elevated numbers of centrosomes (Lingle et al., *Proc. Natl. Acad. Sci. U.S.A.* 99:1978-1983 (2002); Pihan et al., *Cancer Res.* 58:3974-3985 (1998)), although whether centrosome amplification contributes to transformation or is a consequence of cancer progression has not been determined. Because centrosomes usually nucleate microtubules, cells with supernumerary centrosomes form multopolar mitotic spindles and may undergo mitotic catastrophe. (Margottin-Goguet et al., *Dev. Cell* 4:813-826 (2003).

Mitotic catastrophe is loosely defined as a form of cell death that occurs during mitosis and arises from aberrant G2 checkpoint control. Although the molecular details of mitotic catastrophe remain to be defined, several genes involved in the G2 checkpoint induce mitotic castrophe when disrupted, including 14-3-3 σ (Chan et al., *Nature* 401:616-620 (1999)), ATR (Brown and Baltimore, *Gene Dev.* 14:397-402 (2000)), and the CHK1 kinase (Takai et al., *Genes Dev.* 14:1439-1447 (2000)). In addition, defects in proteins required for the mitotic spindle assembly also induce catastrophe. Depletion of hNuf2, a kinetochore protein involved in microtubule attachment, arrests cells in prometaphase and induces mitotic cell death. (DeLuca et al., *J. Cell Biol.* 159:549-555 (2002).

Because mitotic catastrophe is induced in proliferating cells, and also occurs following DNA damage in cells with mutations in checkpoint proteins, induction of catastrophe presents a promising opportunity for specifically targeting cancer cells.

The forkhead box (Fox) family of transcription factors plays important roles in regulating cellular proliferation, differentiation, longevity, and cellular transformation. Wang et al., *Proc. Natl. Acad. Sci. USA* 98:11468-11473 (2001). FOXM1, previously known as HFH-11, Trident, WIN and FKL16, is a Fox transcription factor widely expressed in proliferating cells.

It is suggested that FOXM1 is required for normal S-M phase coupling during cell cycle progression. FOXM1 levels increase at the start of DNA replication and persist until the end of mitosis in cells synchronized by serum starvation. Korver et al., *Nucleic Acids Res.*, 25:1715-1719 (1997). FOXM1 knockout mice exhibit cell division defects including DNA polyploidy in the heart and the liver cells, indicating that expression of FOXM1 is required to prevent multiple rounds of S phase in one cell cycle. Korver et al., *Curr. Biol.*, 8:1327-1330 (1998). Studies of cultured cells demonstrate that over-expression of FOXM1 alters cell cycle kinetics by facilitating progression through G2/M. Leung et al., *FEBS Letters*, 507:59-66 (2001). Moreover, it has been reported that FOXM1 protein and RNA levels were markedly increased throughout the period of lung repair when cells were undergoing extensive proliferation in response to acute lung injury. Kalinichenko et al., *Am. J. Physiol. Lung Cell Mol. Physiol.*, 280:L695-L704 (2001). premature expression of FOXM1 in transgenic mice accelerates hepatocyte DNA replication and the expression of cell cycle regulatory proteins following partial hepatectomy. Ye et al., *Mol. Cell Biol.* 19:8570-8580 (1999). Elevated expression of FOXM1 has been reported in both hepatocellular carcinoma (Okabe et al., *Cancer Res.* 61:2129-2137 (2001)) and in basal cell carcinoma (Teh et al., *Cancer Res.* 62:4773-4780 (2002)). However, whether FOXM1 is essential for cancer cell proliferation has not been determined.

As a transcription factor, FOXM1 may exert its cell cycle regulation function by regulating the expression of other genes. It has been reported that FOXM1 activates the expression of cyclin B1 promoter but not of cyclin D1. Leung et al., *FEBS Letters*, 507:59-66 (2001). Additionally, studies using transgenic mouse models identified genes that are induced in regenerating livers of FOXM1 transgenic mice relative to wild-type control mice. These genes include several immediate early transcription factors (ID-3, Stat3, Nur77), MMP-9, and several stress response genes. Wang, et al., *Gene Expr.,* 11: 149-62 (2003).

On the other hand, FOXM1 is a downstream target of glioma transcription factor-1 (Gli1) in certain cell carcinomas. Teh et al., *Cancer Res.*, 62:4773-4780 (2002). Activation of Sonic Hedgehog (Shh) signaling plays a key role in the development of basal cell carcinomas (BCCs) of the skin in humans. It is reported that FOXM1 levels increase in BCCs and that expression of the Shh target Gli1 caused a significant elevation of FOXM1 mRNA level and transcriptional activation.

Specific gene targeting sheds light on the biological mechanism applied by FOXM1 in cell cycle regulation. In addition, such gene or protein targets may provide new candidates for therapeutics or diagnostics for cell proliferative disorders.

Cancer is a general term for a group of diseases that involve the growth and spreading of abnormal cells in the body. This disease develops when cells continue to grow and divide until they spread to other parts of the body, leading to tumor development and destruction or invasion of normal body tissue. Tumors ultimately form colonies of cells in certain parts of the body. Lung, colon, and breast cancers are among the most common cancer types. Other cancers include ovarian cancer, kidney cancer, skin cancer, Kaposi's sarcoma, esophageal cancer, stomach cancer, leukemia, and lymphoma.

Lung cancer causes more cancer-related deaths than breast cancer, prostate cancer, and colon cancer combined. The American Cancer Society estimates that over 170,000 new cases of lung cancer would be reported by the end of 2003. Lung cancer often begins in the bronchi, but it can appear in any of the parts of the lung. Once the cancer takes root it can spread to the other parts of the body through metastasis. Lung cancer is divided into two major types: small cell and non-small cell. Small cell lung cancer has small cells, but they can spread rapidly throughout the body affecting lymph nodes and other organs such as the brain, the liver and the bones. On the other hand, non-small scale lung cancer makes up nearly 80% of the diagnosis for lung cancer.

Colon cancer is an abnormal growth of cells in the digestive system. It is often called colorectal cancer because it can affect both the colon and the rectum. Colon cancer begins in the layers of tissue found in one of the four sections of the colon and develops slowly over time. It is usually first discovered as a polyp, or a small growth of tissue in the colon. According to American Cancer Society statistics, colon cancer is the third most common type of cancer among men and women. This type of cancer was estimated to affect 105,000 people by the end of 2003.

Breast cancer is a tumor that is originally found in the cells of the breast. It is most common in women, but can also be found in men as well. It is the most common form of cancer among women, other than skin cancer. Every year more than 200,000 women are diagnosed with the disease in the United States alone. It was estimated that, in 2003, nearly 40,000 American women would die of this disease. Women who have been diagnosed with breast cancer have a number of treatment options depending on the stage of the cancer. One of the most important factors about breast cancer is the concept of early detection.

As demonstrated above, cancer is one of the most pervasive diseases in the world today. However, definitive cures have not been established. As a result, innovative methods for treatment are constantly pursued. Indeed, one of the most important ways to control cancer is through early detection methods. The present invention addresses these needs.

SUMMARY OF THE INVENTION

FOXM1 expression is upregulated in cancer cell lines, including, but not limited to, lung, colon, and breast cancer cells, as compared to normal cells. Specifically, the RNA encoding FOXM1 has been found to increase in lung, colon and breast cancer samples as determined from tissue expression profiling data using Affymetrix® GeneChip chips. Moreover, inhibition of FOXM1 expression with RNA interference generates mitotic spindle defects, delays cells in mitosis, and induces mitotic catastrophe. Thus, FOXM1 has been discovered as a target for cancer therapeutics and diagnosis.

Accordingly, one aspect of the invention provides a method for treating a subject that has or is at risk of developing cancer. The method comprises administering to the subject a composition comprising an agent that modulates at least one activity of FOXM1. In one embodiment, the agent decreases the protein activity or protein level of FOXM1. In another embodiment, the agent decreases the mRNA level of FOXM1. In yet another embodiment, the agent is selected from the group consisting of hormones, cytokines, small molecules, antibodies, antisense oligonucleotides, chemicals, and RNA inhibitors such as small hairpin RNA (shRNA), short interference RNA (siRNA) and ribozymes. In some embodiments, the subject being treated has or is at risk of developing lung, colon, or breast cancer.

Another aspect of the invention provides a composition for treating cancer. The composition comprises an agent that inhibits at least one FOXM1 activity. In one embodiment, the agent inhibits the FOXM1 activity by decreasing the protein activity or level of FOXM1. In another embodiment, the agent inhibits the FOXM1 activity by decreasing the mRNA level of FOXM1. In yet another embodiment, the agent is selected from the group consisting of hormones, cytokines, small molecules, antibodies, antisense oligonucleotides, chemicals, and RNA inhibitors. In some embodiments, the composition further comprises a carrier. In some embodiments, the composition is used to treat lung, colon, or breast cancer.

Yet another aspect of the invention provides a method of screening for an agent that modulates the activity of FOXM1. The method comprises exposing a sample (e.g., of tissue, a cell culture, or an amount of FOXM1) to a test agent, detecting a level of activity of FOXM1 and comparing the level of activity of FOXM1 to a control level. In one embodiment, the FOXM1 activity detected and compared is the mRNA level of FOXM1. In another embodiment, the FOXM1 activity detected and compared is the protein activity or level of FOXM1. In yet another embodiment, the FOXM1 activity detected is the promoter activity wherein a reporter construct containing a FOXM1 promoter is used. In other embodiments, constructs having fragments of FOXM1 may be used and the activities of the fragments may be compared to screen for the modulating agents.

Yet another aspect of the invention provides a method of screening for an agent that modulates the FOXM1 signaling pathway. The method comprises exposing a sample to a test agent, detecting a level of activities of at least one FOXM1 pathway target, i.e., FOXM1 or a molecule that is regulated by FOXM1, and comparing the level of activity of the at least one FOXM1 target to a control level. In one embodiment, the FOXM1 target activity detected and compared is the mRNA level of the target molecule. In another embodiment, the FOXM1 target activity detected and compared is the protein activity or level of the target molecule. In yet other embodiments, the FOXM1 target activity detected is the activity or level of a fragment of the target molecule or the promoter activity wherein a reporter construct containing a target molecule promoter is used. The sample used in this aspect of the invention is of tissue or a cell culture or a mixture comprising the FOXM1 target, a fragment of the FOXM1 target, or a reporter having the FOXM1 target promoter. The FOXM1 target is selected from the group consisting of FOXM1, DR1, ZNF302, HMGN4, CIAO1, RBBP1, CDKN3, CDC25B, KIF20A, NEK2, CCNA2, CENPA, BICD2, KIAA1026, DUSP6, CYP1A1, GSR, GNPI, RETSDR2, EREG, IL8, ARHD, RAB5EP, DAPK3, PTPRG, MMD, SSA2, RPL23, PTPN18, TOE1, TP53BPL, F2RL1, FLJ11753, SERPINE1, and UNK_AW575379.

In another aspect, the invention provides molecules that are regulated by FOXM1 in the FOXM1 pathway. These molecules can be used to screen for agents that specifically regulate the FOXM1 pathway.

In another aspect of the invention, a method is provided for determining whether a subject has or is at risk of developing cancer. The method comprises measuring in the subject or in a sample (e.g., of a tissue or a cell culture) obtained from the subject at least one FOXM1 activity and comparing the measured FOXM1 activity to a control activity, wherein an increase in the FOXM1 activity in the subject or the sample relative to the control indicates that the subject has or is at risk of developing cancer. In one embodiment, the FOXM1 activity is determined by measuring the mRNA level of FOXM1. In another embodiment, the FOXM1 activity is determined by measuring the protein level or activity of FOXM1. In some of the embodiments, the method determines whether the subject has or is at risk of developing lung, colon, or breast cancer. In some embodiments, the subject is a mammal. In one embodiment, the subject is a human.

In another aspect, the invention provides a method for decreasing cancer cell proliferation. The method comprises contacting a cancer cell in vitro or in vivo with a composition comprising an agent that modulates at least one FOXM1 activity. In one embodiment, the agent modulates the FOXM1 activity by decreasing the protein level or activity of FOXM1. In another embodiment, the agent modulates the FOXM1 activity by decreasing the mRNA level of FOXM1. In yet another embodiment, the agent is selected from the group consisting of hormones, cytokines, small molecules, antibodies, antisense oligonucleotides, chemicals, and RNA inhibitors. In some embodiments, the method is used to decrease lung, colon, or breast cancer cell proliferation.

In yet another aspect, the invention provides a method for screening molecules that are regulated by FOXM1 that may relate to cell cycle regulation. The screening method comprises: (a) treating cells with a FOXM1 inhibitor, (b) measuring in the cell at least one activity of the molecule being tested, and (c) comparing the activity of the molecule before and after the FOXM1 inhibitor treatment, wherein a change in the activity of the molecule indicates that the molecule is part of the FOXM1 pathway for cell cycle regulation. In one embodiment, the activity of molecule is determined by measuring the mRNA level of the molecule. In another embodiment, the activity of the molecule is determined by measuring the protein activity or protein level of the molecule. In some embodiments, the FOXM1 inhibitor is selected from the group consisting of hormones, cytokines, small molecules, antibodies, antisense oligonucleotides, chemicals, and RNA inhibitors.

DESCRIPTION OF THE FIGURES

FIG. 1 is a graphic representation that demonstrates the transcriptional profiling data from primary lung, colon, and breast cancer and adjacent normal tissues.

FIG. 2A is a graphic representation that demonstrates the transcriptional profiling data of FOXM1 from normal breast tissue (N), fibrocystic breast (FC), fibroadenomas (FA), and infiltrating ductal carcinomas (IDC). FIG. 2B is a graphic representation that demonstrates the mRNA levels of FOXM1 in tumor tissue (T) and adjacent normal tissue (N). FIG. 2C is photographic representation of Western blot analysis that shows the level of FOXM1 protein in various cell lines. Beta-actin was used as a loading control.

FIG. 3A is a photographic representation of Western blot analysis that shows the level of FOXM1 protein expression in BT-20 cells after FOXM1 siRNA treatment. FIG. 3B is a photographic representation of Western blot analysis that shows the level of FOXM1 protein expression in MCF-7 cells after FOXM1 siRNA treatment.

FIG. 4A is a graphic representation of the experimental timeline for FIGS. 4-9. FIG. 4B is graphic representation of Taqman® analysis of FOXM1 RNA level and a photographic representation of Western blot analysis of FOXM1 protein level after FOXM1 shRNA treatment.

FIGS. 5A-5C are photographic representations of time-lapse microscopy of mitotic BT-20 cells stably transfected with control shRNA (FIG. 5A) or FOXM1 shRNA (FIGS. 5B and 5C). FIG. 5D are photographic representations of phase contrast images of BT-20 cells three weeks after transfection with control shRNA or FOXM1 shRNA. FIG. 5E is a photographic representation of analysis of BrdU (5-bromo-2'-deoxyuridine) incorporation by cells treated with control shRNA or FOXM1 shRNA. Cells were labeled with BrdU for 20 hours and stained with anti-BrdU antibody (green) and counterstained with DAPI (4', 6-Diamidino-2-phenylindole, dihydrochloride) (blue). All images are at the same magnification.

FIG. 6 is a photographic representation of mitotic catastrophe in cells transfected with FOXM1 shRNA. For analysis, cells were fixed, stained with DAPI, and analyzed by phase contrast or fluorescence microscopy.

FIG. 7 is a photographic representation of cells with enlarged nuclei after transfection with FOXM1 shRNA. Cells were fixed, stained with DAPI, and photographed at the same magnification.

FIGS. 8A-8D are photographic representations of mitotic spindle abnormalities in BT-20 cells treated with control shRNA (FIG. 8A) or FOXM1 shRNA (FIGS. 8B-8D). The first column shows staining for microtubules with anti-α-tubulin antibody, the second column is DNA stained with DAPI, and the third column is a merged image.

FIGS. 9A-9E are photographic representations of centrosomal amplification of cells treated with control shRNA (FIG. 9A) or FOXM1 shRNA (FIGS. 9B-9E). Cells were stained with monoclonal antibody to γ-tubulin. The first column shows centrosomes, the second column shows DNA, and the third column is a merged image. White arrows indicate centrosomes that are not functioning as microtubule organizing centers.

FIG. 10 is a chart that lists genes regulated by treatment with FOXM1 siRNA and demonstrates the levels of regulation.

DETAILED DESCRIPTION OF THE INVENTION

Figure 1:
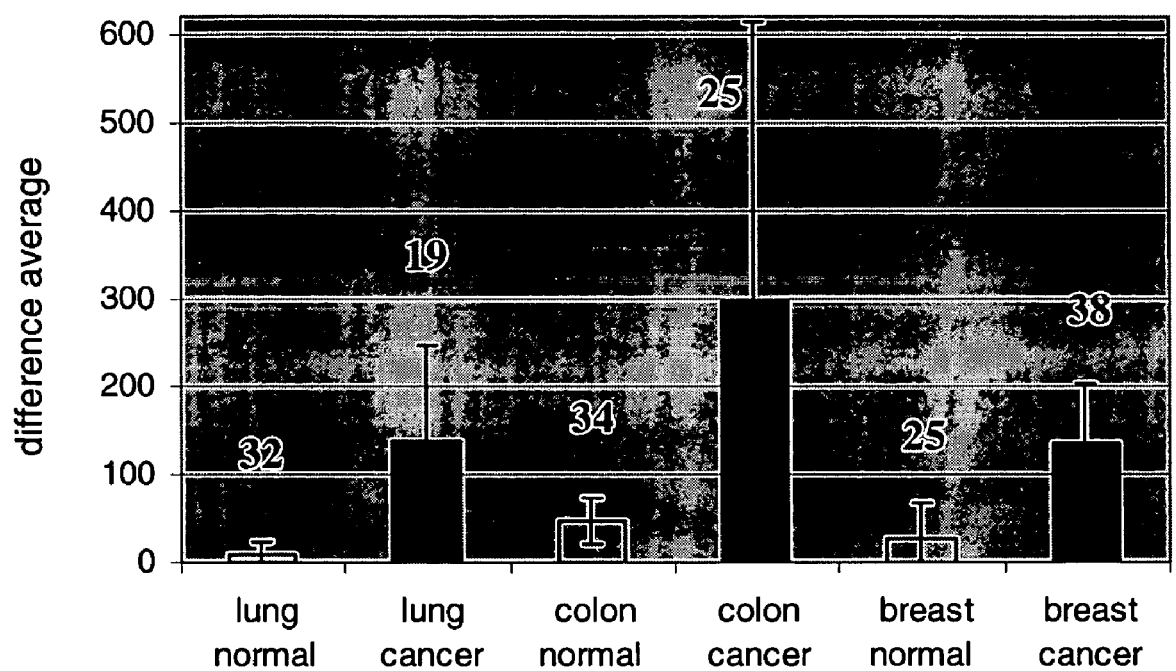
FIG. 1.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The patent and scientific literature referred to herein establishes knowledge that is available to those of skill in the art. The issued U.S. patents, allowed applications, published applications (U.S. and foreign) and references, including GenBank® database sequences, that are cited herein are incorporated by reference to the same extent as if each was specifically and individually indicated to be incorporated by reference.

The invention is based upon the unexpected discovery that FOXM1 is unregulated in cancer cells, including, but not limited to, lung, colon, and breast cancers, as compared to normal cells. Specifically, the RNA encoding FOXM1 has been found to increase in lung, colon, or breast cancer samples. Additionally, FOXM1 expression is elevated in hepatocellular carcinoma and basal cell carcinoma. Moreover, inhibition of FOXM1 expression with RNA interference delays cells in mitosis and induces mitotic spindle defects, centrosome amplification, polyploidy, and mitotic catastrophe. These findings indicate that FOXM1 is essential for tumor cell proliferation and suggest that FOXM1 coordinates the expression of genes required for transcriptional regulation, cell cycle control, and chromosome segregation. Furthermore, these findings present FOXM1 and molecules in the FOXM1 pathway as therapeutic and diagnostic opportunities to cancer.

As used herein, "lung cancer" is the disease that involves uncontrolled cell growth in the lung and includes squamous cell carcinoma and adenocarcinoma of the lung "Colon cancer" is the disease that involves uncontrolled cell growth in the colon and includes adenocarcinoma of the colon. "Breast cancer" is the disease that involves uncontrolled cell growth in the breast, including infiltrating ductal carcinoma of the breast and infiltrating lobular carcinoma of the breast.

In one embodiment of the invention, expression of FOXM1 is studied using expression profiling data. In another embodiment, the RNA levels are determined by mRNA hybridization to Affymetrix® HGU95A chips. In another embodiment of the invention, protein levels of FOXM1 are determined using FOXM1 specific antibodies. Both RNA and protein level analyses show increased expression of FOXM1 in cancerous cells. Thus, FOXM1 has been discovered as a target for cancer therapeutics. Further, FOXM1 expression can be correlated with abnormal cell growth for diagnostic purposes.

Expression studies were performed to analyze FOXM1 RNA expression in human cancer cells as well as in normal tissue cells. The results indicated that FOXM1 expression was increased in all of the cancer cells tested in comparison to the normal cells. Thus, the inventors have demonstrated that FOXM1 is involved in cancers, and, consequently, that the expression level of FOXM1 can be used to diagnose cells or tissue of abnormal growth. Additionally, the inventors have demonstrated that an agent that modulates FOXM1 activity, including protein or RNA expression level of FOXM1, will be effective in treating a subject that has or is at risk of developing cancer. "Modulate" as used herein refers to activating or inhibiting or otherwise regulating or adjusting the level or degree of the thing being modulated. As used herein "activity" refers to a function of the FOXM1 DNA, RNA, protein, or a fragment of such, and includes expression of FOXM1. As used herein "expression" refers to the level of mRNA or protein in a cell produced from the FOXM1 gene, including the level of transcription of the DNA or translation of the mRNA.

In one aspect, the invention provides a method of screening for or diagnosing cancer in a patient. In another aspect, the invention provides a method of screening for an increase in activity of FOXM1 in a patient, including an increase in FOXM1 protein activity or FOXM1 protein or RNA expression. By way of nonlimiting example, the screening method can include obtaining a sample of tissue from the patient, preparing a composition of cellular material from the sample (which in some embodiments may involve various extraction or isolation steps to extract or isolate, for example, RNA or protein from the cellular material), detecting the level of FOXM1 protein or RNA in the composition of cellular material, and comparing the level of FOXM1 protein or RNA in the composition of cellular material to a control level. In another nonlimiting example, these methods can include exposing a tissue or cell sample from the patient to an agent that binds to FOXM1, detecting the level of FOXM1 in the sample, and comparing the FOXM1 in the sample to a control level. If the level of binding of the agent to FOXM1 is increased relative to the control level, the patient may be classified as having or is at risk of developing cancer. Nonlimiting examples of agents useful in this method include antibodies or siRNA directed against FOXM1 as described herein. Nonlimiting examples of cancers that can be tested by this method include lung, colon, and breast cancer.

Another aspect of the invention provides a method of testing abnormal growth in a cell. The method comprises measuring in the cell at least one FOXM1 activity and comparing the measured FOXM1 activity to a control activity, wherein an increase in the FOXM1 activity in the tested cell relative to the control indicates that the cell is subject to or at risk of abnormal growth. In one embodiment, the FOXM1 activity is determined by measuring the mRNA level of FOXM1. In another embodiment, the FOXM1 activity is determined by measuring the protein level of FOXM1. In some of the embodiments, the cell is from lung, colon, or breast tissue of a mammal.

The invention also provides a method of screening for agents for treating cancer. This method can be practiced by screening for an agent that modulates (e.g., inhibits or activates) an activity of FOXM1 such as the mRNA level of FOXM1 or the protein activity or level of FOXM1. As used herein, "agent" includes, but is not limited to, synthetic small molecules, chemicals, nucleic acids such as antisense oligonucleotides, RNA inhibitors such as shRNA, siRNA and ribozymes, peptides and proteins such as hormones, cytokines, antibodies and portions thereof. In one aspect, the methods include contacting a sample of tissue or cells in which FOXM1 is expressed or contacting FOXM1 with a test agent. In one aspect, the test agent is one that is thought to be effective in modulating (e.g., inhibiting or increasing) the activity or expression of FOXM1. A "test agent" is a putative "agent," the modulating ability of which has not yet been confirmed. Once test agents are screened, they are classified as "agents" if they are shown to modulate activity (for example, by inhibiting or activating or otherwise affecting the signal pathway) or expression (for example, by modulating transcription or translation). Accordingly, in additional embodiments, the agent may modify FOXM1 transcription, FOXM1 translation, or the FOXM1 signal pathway. In a particular embodiment, the agent reduces or inhibits the activity or expression of FOXM1. In some embodiments the agent binds to FOXM1. In other embodiments the agent interacts with FOXM1. In still other embodiments, the agent binds to or interacts with (such as by chemically modifying) an inhibitor or activator of FOXM1 activity or expression. By way of nonlimiting example, an agent may bind to and inhibit an activator of FOXM1 or an agent may bind to and activate an inhibitor of FOXM1 activity.

The methods include: exposing a sample (e.g., of tissue, a cell culture, or an amount of FOXM1) to a test agent, detecting a level of activity or expression of FOXM1 and comparing the level of activity or expression of FOXM1 to a control level. The level of activity or expression of FOXM1 may be increased or decreased relative to the control level. If the test agent reduces or inhibits the activity or expression of the FOXM1, then it may be classified as an agent for treating cancer. Exemplary agents that inhibit the activity or expression of FOXM1 include, without limitation, FOXM1 antibodies, siRNA, small molecule chemical inhibitors, antisense oligonucleotides, and ribozymes.

A control level can be determined by any method known in the art. By way of nonlimiting example, a control level includes standard levels or normal levels of FOXM1 in a normal cell. Such standard levels can be determined by testing the level of FOXM1 in a specific tissue (which corresponds to the tissue being tested in the method) from a variety of subjects without cancer or any abnormal cell growth. An average of these levels can be used as the control level. If tissues from different animals are used, standard levels can be determined for each animal species or for a group of animal species. In addition, a control level may refer to the level measured from a sample to which the experimental element, i.e., the test agent, was not applied in an experiment.

The gene for FOXM1 is located at chromosome location 12p13. FOXM1's GenBank® accession number is U74613. The discovery that elevated FOXM1 is associated with cancer or abnormal cell growth renders the sequences of FOXM1 useful in methods of identifying agents of the invention. Such methods include assaying potential agents for the ability to modulate FOXM1 activity or expression. Polynucleotides and polypeptides useful in these assays include not only the genes and encoded polypeptides disclosed herein, but also variants thereof that have substantially the same activity as wild-type genes and polypeptides. "Variants" as used herein, include polynucleotides or polypeptides containing one or more deletions, insertions or substitutions, as long as the variant retains substantially the same activity of the wild-type polynucleotide or polypeptide. With regard to polypeptides, deletion variants are contemplated to include fragments lacking portions of the polypeptide not essential for biological activity, and insertion variants are contemplated to include fusion polypeptides in which the wild-type polypeptide or fragment thereof has been fused to another polypeptide.

The FOXM1 protein sequence can be found in GenBank® under accession number U74613. The deposited protein sequence, as revised on Oct. 21, 2002 (according to GenBank® database), is:

(SEQ ID NO: 7)
MKTSPRRPLILKRRRLPLPVQNAPSETSEEEPKRSPAQQESNQAEASKEV
AESNSCKFPAGIKIINHPTMPNTQVVAIPNNANIHSIITALTAKGKESGS
SGPNKFILISCGGAPTQPPGLRPQTQTSYDAKRTEVTLETLGPKPAARDV
NLPRPPGALCEQKRETCADGEAAGCTINNSLSNIQWLRKMSSDGLGSRSI
KQEMEEKENCHLEQRQVKVEEPSRPSASWQNSVSERPPYSYMAMIQFAIN
STERKRMTLKDIYTWIEDHFPYFKHIAKPGWKNSIRHNLSLHDMFVRETS
ANGKVSFWTIHPSANRYLTLDQVFKQQKRPNPELRRNMTIKTELPLGARR
KMKPLLPRVSSYLVPIQFPVNQSLVLQPSVKVPLPLAASLMSSELARHSK
RVRIAPKVLLAEEGIAPLSSAGPGKEEKLLFGEGFSPLLPVQTIKEEEIQ
PGEEMPHLARPIKVESPPLEEWPSPAPSFKEESSHSWEDSSQSPTPRPKK
SYSGLRSPTRCVSEMLVIQHRERRERSRSRRKQHLLPPCVDEPELLFSEG
PSTSRWAAELPFPADSSDPASQLSYSQEVGGPFKTPIKETLPISSTPSKS
VLPRTPESWRLTPPAKVGGLDFSPVQTSQGASDPLPDPLGLMDLSTTPLQ
SAPPLESPQRLLSSEPLDLISVPFGNSSPSDIDVPKPGSPEPQVSGLAAN
RSLTEGLVLDTMNDSLSKILLDISFPGLDEDPLGPDNINWSQFIPELQ.

The FOXM1 nucleic acid sequence can be found in GenBank® under accession number U74613. The deposited FOXM1 nucleic acid sequence, as revised on Oct. 21, 2002 (according to GenBank® database), is:

```
  1 ggagcccgga gcccgccttc ggagctacgg cctaacggcg gcggcgactg cagtctggag    (SEQ ID NO: 8)
 61 ggtccacact tgtgattctc aatggagagt gaaaacgcag attcataatg aaaactagcc
121 cccgtcggcc actgattctc aaaagacgga ggctgcccct tcctgttcaa aatgccccaa
181 gtgaaacatc agaggaggaa cctaagagat cccctgccca acaggagtct aatcaagcag
241 aggcctccaa ggaagtggca gagtccaact cttgcaagtt tccagctggg atcaagatta
301 ttaaccaccc caccatgccc aacacgcaag tagtggccat ccccaacaat gctaatattc
361 acagcatcat cacagcactg actgccaagg gaaagagag tggcagtagt gggcccaaca
421 aattcatcct catcagctgt gggggagccc caactcagcc tccaggactc cggcctcaaa
481 cccaaaccag ctatgatgcc aaaaggacag aagtgaccct ggagaccttg ggaccaaaac
541 ctgcagctag ggatgtgaat cttcctagac cacctggagc cctttgcgag cagaaacggg
601 agacctgtgc agatggtgag gcagcaggct gcactatcaa caatagccta tccaacatcc
661 agtggcttcg aaagatgagt tctgatggac tgggctcccg cagcatcaag caagagatgg
721 aggaaaagga gaattgtcac ctggagcagc gacaggttaa ggttgaggag ccttcgagac
781 catcagcgtc ctggcagaac tctgtgtctg agcggccacc ctactcttac atggccatga
841 tacaattcgc catcaacagc actgagagga agcgcatgac tttgaaagac atctatacgt
901 ggattgagga ccactttccc tactttaagc acattgccaa gccaggctgg aagaactcca
```

-continued

```
 961 tccgccacaa cctttccctg cacgacatgt ttgtccggga gacgtctgcc aatggcaagg
1021 tctccttctg gaccattcac cccagtgcca accgctactt gacattggac caggtgttta
1081 agcagcagaa acgaccgaat ccagagctcc gccggaacat gaccatcaaa accgaactcc
1141 ccctgggcgc acggcggaag atgaagccac tgctaccacg ggtcagctca tacctggtac
1201 ctatccagtt cccggtgaac cagtcactgg tgttgcagcc ctcggtgaag gtgccattgc
1261 ccctggcggc ttccctcatg agctcagagc ttgcccgcca tagcaagcga gtccgcattg
1321 cccccaaggt gctgctagct gaggagggga tagctcctct ttcttctgca ggaccaggga
1381 aagaggagaa actcctgttt ggagaagggt tttctccttt gcttccagtt cagactatca
1441 aggaggaaga aatccagcct ggggaggaaa tgccacactt agcgagaccc atcaaagtgg
1501 agagccctcc cttggaagag tggccctccc cggccccatc tttcaaagag gaatcatctc
1561 actcctggga ggattcgtcc caatctccca ccccaagacc caagaagtcc tacagtgggc
1621 ttaggtcccc aacccggtgt gtctcggaaa tgcttgtgat tcaacacagg gagaggaggg
1681 agaggagccg gtctcggagg aaacagcatc tactgcctcc ctgtgtggat gagccggagc
1741 tgctcttctc agaggggccc agtacttccc gctgggccgc agagctcccg ttcccagcag
1801 actcctctga ccctgcctcc cagctcagct actcccagga agtgggagga ccttttaaga
1861 cacccattaa ggaaacgctg cccatctcct ccaccccgag caaatctgtc ctccccagaa
1921 cccctgaatc ctggaggctc acgcccccag ccaaagtagg gggactggat ttcagcccag
1981 tacaaacctc ccagggtgcc tctgacccct tgcctgaccc cctggggctg atggatctca
2041 gcaccactcc cttgcaaagt gctccccccc ttgaatcacc gcaaaggctc ctcagttcag
2101 aacccttaga cctcatctcc gtcccctttg gcaactcttc tccctcagat atagacgtcc
2161 ccaagccagg ctccccggag ccacaggttt ctggccttgc agccaatcgt tctctgacag
2221 aaggcctggt cctggacaca atgaatgaca gcctcagcaa gatcctgctg gacatcagct
2281 ttcctggcct ggacgaggac ccactgggcc ctgacaacat caactggtcc cagtttattc
2341 ctgagctaca gtagagccct gcccttgccc ctgtgctcaa gctgtccacc atcccgggca
2401 ctccaaggct cagtgcaccc caagcctctg agtgaggaca gcaggcaggg actgttctgc
2461 tcctcatagc tccctgctgc ctgattatgc aaaagtagca gtcacaccct agccactgct
2521 gggaccttgt gttccccaag agtatctgat tcctctgctg tccctgccag gagctgaagg
2581 gtgggaacaa caaaggcaat ggtgaaaaga gattaggaac ccccagcct gtttccattc
2641 tctgcccagc agtctcttac cttccctgat cttttgcaggg tggtccgtgt aaatagtata
2701 aattctccaa attatcctct aattataaat gtaagcttat ttccttagat cattatccag
2761 agactgccag aaggtgggta ggatgacctg gggtttcaat tgacttctgt tccttgcttt
2821 tagtttttgat agaagggaag acctgcagtg cacggtttct tccaggctga ggtacctgga
2881 tcttgggttc ttcactgcag ggacccgac aagtggatct gcttgccaga gtccttttg
2941 cccctccctg ccacctcccc gtgtttccaa gtcagctttc ctgcaagaag aaatcctggt
3001 taaaaaagtc ttttgtattg ggtcaggagt tgaatttggg gtgggaggat ggatgcaact
3061 gaagcagagt gtgggtgccc agatgtgcgc tattagatgt ttctctgata atgtccccaa
3121 tcataccagg gagactggca ttgacgagaa ctcaggtgga ggcttgagaa ggccgaaagg
3181 gcccctgacc tgcctggctt ccttagcttg cccctcagct ttgcaaagag ccaccctagg
3241 ccccagctga ccgcatgggt gtgagccagc ttgagaacac taactactca ataaaagcga
3301 aggtggacaa aaaaaaaaaa aaaaaa.
```

Accordingly, the FOXM1 in the invention may be encoded by a nucleotide sequence that has at least about 60%, at least about 70%, at least about 80% or at least about 90% identity to the FOXM1 nucleotide sequence set forth in GenBank® accession number U74613, which is incorporated by reference.

Additionally, the FOXM1 protein may be encoded by nucleotide sequences having substantial similarity to the nucleotide sequence set forth in GenBank® accession number U74613. "Substantial similarity," as used herein means that the nucleotide sequence is sufficiently similar to a reference nucleotide sequence that it will hybridize therewith under moderately stringent conditions. This method of determining similarity is well known in the art to which the invention pertains. Examples of stringency conditions are shown in Table 1 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 1

| Stringency Condition | Poly-nucleotide Hybrid | Hybrid Length (bp)[1] | Hybridization Temperature and Buffer[2] | Wash Temperature and Buffer[2] |
|---|---|---|---|---|
| A | DNA:DNA | >50 | 65° C.; 1× SSC -or- 42° C.; 1× SSC, 50% formamide | 65° C.; 0.3× SSC |
| B | DNA:DNA | <50 | $T_B$*; 1× SSC | $T_B$*; 1× SSC |
| C | DNA:RNA | >50 | 67° C.; 1× SSC -or- 45° C.; 1× SSC, 50% formamide | 67° C.; 0.3× SSC |
| D | DNA:RNA | <50 | $T_D$*; 1× SSC | $T_D$*; 1× SSC |
| E | RNA:RNA | >50 | 70° C.; 1× SSC -or- 50° C.; 1× SSC, 50% formamide | 70° C.; 0.3× SSC |
| F | RNA:RNA | <50 | $T_F$*; 1× SSC | $T_F$*; 1× SSC |
| G | DNA:DNA | >50 | 65° C.; 4× SSC -or- 42° C.; 4× SSC, 50% formamide | 65° C.; 1× SSC |
| H | DNA:DNA | <50 | $T_H$*; 4× SSC | $T_H$*; 4× SSC |
| I | DNA:RNA | >50 | 67° C.; 4× SSC -or- 45° C.; 4× SSC, 50% formamide | 67° C.; 1× SSC |
| J | DNA:RNA | <50 | $T_J$*; 4× SSC | $T_J$*; 4× SSC |
| K | RNA:RNA | >50 | 70° C.; 4× SSC -or- 50° C.; 4× SSC, 50% formamide | 67° C.; 1× SSC |
| L | RNA:RNA | <50 | $T_L$*; 2× SSC | $T_L$*; 2× SSC |
| M | DNA:DNA | >50 | 50° C.; 4× SSC -or- 40° C.; 6× SSC, 50% formamide | 50° C.; 2× SSC |
| N | DNA:DNA | <50 | $T_N$*; 6× SSC | $T_N$*; 6× SSC |
| O | DNA:RNA | >50 | 55° C.; 4× SSC -or- 42° C.; 6× SSC, 50% formamide | 55° C.; 2× SSC |
| P | DNA:RNA | <50 | $T_P$*; 6× SSC | $T_P$*; 6× SSC |
| Q | RNA:RNA | >50 | 60° C.; 4× SSC -or- 45° C.; 6× SSC, 50% formamide | 60° C.; 2× SSC |
| R | RNA:RNA | <50 | $T_R$*; 4× SSC | $T_R$*; 4× SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can bedetermined by aligning the sequences of the polynucleotides and identifying the region or regions of optimal sequence complementarity.
[2]SSPE (1× SSPE is 0.15 M NaCl, 10 mM NaH$_2$PO$_4$, and 1.25 mM EDTA, pH 7.4) can be substituted for SSC (1× SSC is 0.15 M NaCl and 15 mM sodium citrate) in the hybridization and wash buffers; washes are performed for 15 minutes after hybridization is complete.
$T_B$*–$T_R$*: The hybridization temperature for hybrids anticipated to be less than 50 base pairs in length should be 5–10 EC less than the melting temperature ($T_m$) of the hybrid, where $T_m$ is determined according to the following equations. For hybrids less than 18 base pairs inlength, $T_m$(EC) = 2(# of A + T bases) + 4(# of G + C bases). For hybrids between 18 and 49 base pairs in length, $T_m$(EC) = 81.5 + 16.6($\log_{10}$Na+) + 0.41(% G + C) − (600/N), where N is the number of bases in the hybrid, and Na+ is the concentration of sodium ions in the hybridization buffer (Na+ for 1× SSC = 0.165 M).

Additional examples of stringency conditions for polynucleotide hybridization are provided in Sambrook et al., "Molecular Cloning: A Laboratory Manual", Chs. 9 & 11, Cold Spring Harbor Laboratory Press, Cold Spring Harbor, N.Y. (1989), and Ausubel et al., eds., *Current Protocols in Molecular Biology*, §§2.10, 6.3-6.4, John Wiley & Sons, Inc. (1995), herein incorporated by reference.

FOXM1 may be produced by methods known to the skilled artisan. For example, a nucleotide sequence encoding the FOXM1 gene may be introduced into a desired host cell. Such a nucleotide sequence may first be inserted into an appropriate recombinant expression vector.

Recombinant expression vectors may be constructed by incorporating the above-recited nucleotide sequences within a vector according to methods well known to the skilled artisan. A wide variety of vectors are known that are useful in the invention. Suitable vectors include plasmid vectors and viral vectors, including retrovirus vectors, adenovirus vectors, adeno-associated virus vectors and herpes viral vectors. The vectors may include other known genetic elements necessary or desirable for efficient expression of the nucleic acid in a specified host cell, including regulatory elements. For example, the vectors may include a promoter and any necessary enhancer sequences that cooperate with the promoter to achieve transcription of the gene. The nucleotide sequence may be operably linked to such regulatory elements.

Such a nucleotide sequence is referred to as a "genetic construct." A genetic construct may contain a genetic element on its own or in combination with one or more additional genetic elements, including but not limited to genes, promoters, or enhancers. In some embodiments, these genetic elements are operably linked. In some embodiments, the specific gene at issue (e.g., FOXM1) may not be present in the genetic construct, including, but not limited to, a situation in which a FOXM1 promoter is operably linked to a reporter gene.

As used herein, a nucleotide sequence is "operably linked" to another nucleotide sequence when it is placed in a functional relationship with another nucleotide sequence. For example, if a coding sequence is operably linked to a promoter sequence, this generally means that the promoter may modulate (e.g., promote) transcription of the coding sequence, or if a ribosome binding site is operably linked to a coding sequence, this generally means that it is positioned so as to facilitate translation. "Operably linked" means that the DNA sequences being linked are typically contiguous and, where necessary to join two protein coding regions, contiguous and in reading frame. However, since enhancers may function when separated from the promoter by several kilobases and intron sequences may be of variable lengths, some nucleotide sequences may be operably linked but not contiguous or not in reading frame. In some embodiments, linking can be accomplished by ligation at convenient binding sites, or if such sites do not exist, synthetic oligonucleotide adaptors or linkers can be used in accord with conventional practice.

A wide variety of methods are available for introducing the nucleotide sequence encoding FOXM1 or FOXM1 fragments, and which may be included in a recombinant expression vector, into a host cell. Such methods are known to the art and include mechanical methods, chemical methods, lipophilic methods and electroporation. Microinjection and use of a gene gun with, for example, a gold particle substrate for the DNA to be introduced is a representative, non-limiting exemplary mechanical method. Use of calcium phosphate or DEAE-Dextran is a representative, non-limiting exemplary chemical method. Exemplary lipophilic methods include use of liposomes and other cationic agents for lipid-mediated transfection. Such methods are well known to the art.

A wide variety of host cells may be utilized in the present invention to produce FOXM1 and screen for agents that modulate FOXM1. Such cells include, but are not limited to, eukaryotic and prokaryotic cells, including mammalian cells known to the art.

The sample (e.g., tissue, cell culture, or an amount of FOXM1 protein) is typically contacted with a test agent for a time period sufficient to inhibit the activity or expression of the FOXM1. This time period and the quantity of sample may vary depending on factors including, but not limited to, the nature of the inhibitor, the activity/expression detection mechanism and the sample tissue selected. The skilled artisan without undue experimentation may readily determine such times and amounts. An exemplary test agent is one that binds to or otherwise decreases the activity or expression of FOXM1, although test agents that inhibit the activity or expression by, for example, binding to a component of the signal pathway, such as an enzyme substrate, or by some other mechanism, are also envisioned. When a sample tissue is used, the type of tissue chosen may vary depending on the specific cancer being studied. Nonlimiting examples of sample tissues include lung, colon, and breast cancer tissue.

A wide variety of assays may be utilized to determine whether the test agent modulates (e.g., inhibits or activates) the protein activity or expression of FOXM1. For example, if the test agent binds to or interacts with FOXM1 directly, the amount of reactants remaining and/or products formed in the reactions may be quantified. To this end, the amount of reactants remaining after contacting the sample tissue or FOXM1 with the test agent as a function of time may be determined. Similarly, the amount of products produced after contacting the sample tissue or FOXM1 with the test agent as a function of time may be determined. Various assays may be used to determine the quantity of these products and/or reactants.

For example, assays known to one of skill in the art, including but not limited to Northern blots (to determine RNA expression levels) and Western blots (to determine protein expression levels) can be used to determine the level of expression of FOXM1 by measuring the relative amounts of RNA or protein in the sample compared to a control. Other methods of quantitating FOXM1 known to the art include use of various immunoassays, such as enzyme-linked immunosorbents assays, quantitative PCR, or immunohistochemistry.

A wide variety of test agents may be tested in the screening methods of the present invention. For example, small molecule compounds, known in the art, including but not limited to synthetic small molecules, chemicals, antisense oligonucleotides, RNA inhibitors, peptides and proteins such as hormones, cytokines, antibodies and portions thereof, may act as test agents. Additionally, rational drug design based on the structure of FOXM1 or its known ligands or inhibitors can be used to identify new test agents, such as by making alterations in the structure of a known inhibitor.

In one embodiment, the invention provides a method of screening for agents for treating cancer in a mammal by screening for an agent that modulates (e.g., inhibits or activates) the activity of FOXM1, including the expression level of FOXM1. The method includes contacting a nucleotide sequence encoding a reporter gene product operably linked to a FOXM1 promoter, with a test agent thought to be effective in inhibiting production of FOXM1; determining if the test agent inhibits or activates production of the reporter gene product; and classifying the test agent as an agent for treating cancer or regulating cell growth if the test agent modulates (e.g., inhibits or activates) production of the reporter gene product. A wide variety of reporter genes may be operably linked to the FOXM1 promoter described above. Such genes may encode, for example, luciferase, β-galactosidase, chloramphenical acetyltransferase, β-glucuronidase, alkaline phosphatase, and green fluorescent protein, or other reporter gene products known to the art.

The above methods and procedures can also be used for various other screening methods. The invention also provides a method for screening for agents that regulate cell cycle in response to FOXM1. Such screening method comprises treating cells with a FOXM1 inhibitor, measuring at least one activity of a molecule in the cells, and comparing the activity of the molecule before and after the FOXM1 inhibitor treatment. A change in the activity of the molecule indicates that the molecule is part of the FOXM1 pathway for cell cycle regulation. In one embodiment, the activity of molecule is determined by measuring the mRNA level of the molecule. In another embodiment, the activity of the molecule is determined by measuring the protein level or activity of the molecule. In some embodiments, the FOXM1 inhibitor is selected from the group consisting of hormones, cytokines, small molecules, antibodies, antisense oligonucleotides, chemicals, and RNA inhibitors.

In one screening method, stable cell lines expressing elevated levels of FOXM1 are generated. These FOXM1 cell lines are then compared with other cell lines expressing known oncogenes, such as ras, myc, or bcl-2. Potential inhibitors can then be screened for compounds that specifically inhibit growth of cells expressing elevated FOXM1, but do not inhibit growth of cells expressing myc or ras. Thus, a FOXM1 specific inhibitor can be identified.

In another screening method, the promoter of a FOXM1 target, which includes FOXM1 or a molecule that is regulated by FOXM1, can be cloned upstream of a report gene, such as luciferase. The reporter gene can then be stably transfected into cells, and the cells are analyzed for agents, including any molecule or compound, that inhibit expression of the reporter gene. Through the use of multiple cell lines with different reporter genes, inhibitor specificity can be achieved by screening for agents that inhibit several or all of the FOXM1 targets. Moreover, all of the methods described, such as methods for screening for an agent that modulates the activity of FOXM1, a FOXM1 fragment, or the FOXM1 promoter, can be used for other FOXM1 targets. Thus, an agent can be screen for its effect on FOXM1 and another FOXM1 target, a FOXM1 fragment and another FOXM1 target fragment, and the promoters of FOXM1 and other FOXM1 targets.

The invention also provides methods for treating cancer. "Treatment", "treating" or "treated" as used herein, means preventing, reducing or eliminating at least one symptom or complication of cancer. Exemplary symptoms and/or complications of cancer include, but are not limited to, abnormal cell growth, reduced cell death, and metastasis of cancer cells from the primary tumor. These methods include administering to a subject in need thereof a composition comprising an agent that modulates the activity of FOXM1. In one embodiment, the subject is a human. In one embodiment, this comprises administering a therapeutic amount of an agent that decreases the activity of FOXM1, such as the protein activity or the protein or RNA level of FOXM1. A "therapeutic amount" represents an amount of an agent that is capable of inhibiting or decreasing the activity or expression of FOXM1 or causing a clinically significant response. The clinical response includes an improvement in the condition treated or in the prevention of the condition. The particular dose of the agent administered according to this invention will, of course, be determined by the particular circumstances surrounding the case, including the agent administered, the particular cancer being treated and similar conditions. In some embodiments, the agent interacts with FOXM1. In one embodiment, the agent is an inhibitor of FOXM1. In other embodiments, the agent interacts with FOXM1 DNA or RNA. In still other embodiments, the agent binds to or interacts with (such as by chemically modifying) an inhibitor or activator of FOXM1 activity or expression. By way of nonlimiting example, an agent may bind to and inhibit an activator of FOXM1 or an agent may bind to and activate an inhibitor of FOXM1 activity.

Agents that decrease the activity or expression of FOXM1 include those agents discovered in the screening assays described herein, including, but not limited to, FOXM1 antibodies, siRNA, small molecule chemical inhibitors, antisense oligonucleotides, and ribozymes. An antibody as used herein may be, without limitation, a polyclonal antibody, a monoclonal antibody, a chimeric antibody, a humanized antibody, a genetically engineered antibody, a bispecific antibody, antibody fragments (including, but not limited to, "Fv," "F(ab')$_2$," "F(ab)," and "Dab") and single chains representing the reactive portion of the antibody. Such an antibody includes antibodies belonging to any of the immunoglobulin classes, such as IgM, IgG, IgD, IgE, IgA or their subclasses or mixtures thereof. The invention further includes derivates of these antibodies, such as those that retain their FOXM1-binding activity while altering one or more other properties related to their use as a pharmaceutical agent, e.g., serum stability or efficiency of production.

In various embodiments, such an antibody binds to FOXM1, an activator of FOXM1 activity or expression, or another component of the FOXM1 signal pathway. In additional embodiments, the antibody binds an inhibitor of FOXM1 activity or expression. Methods for production of each of the above antibody forms are well known to the art.

Cells that can be used to synthesize antibodies include animal, fungal, bacterial cells or yeast cells after transformation. By way of nonlimiting example, hybridoma cells can be produced in a known manner from animals immunized with FOXM1 and isolation of their antibody-producing B cells, selecting these cells for FOXM1-binding antibodies and subsequently fusing these cells to, for example, human or animal, for example, mouse mylenoma cells, human lymphoblastoid cells or heterohybridoma cells or by infecting these cells with appropriate viruses to produce immortalized cell lines.

By way of nonlimiting example, human FOXM1 monoclonal antibodies may be used to detect FOXM1 or treating a subject with abnormal cell growth. The term "monoclonal" indicates that the character of the antibody obtained is from a substantially homogeneous population of antibodies (i.e., the individual antibodies comprising the population are identical except for possible naturally occurring mutations that may be present in minor amounts), and is not to be construed as requiring production of the antibody by any particular method.

Thus, the detection or quantification of the FOXM1 in a sample can be carried out by an immunoassay utilizing the specific binding reaction between the monoclonal antibody and FOXM1. Various immunoassays are well-known in the art and any of them can be employed. Examples of the immunoassays include sandwich method employing the monoclonal antibody and another monoclonal antibody as primary and secondary antibodies, respectively, sandwich methods employing the monoclonal antibody and a polyclonal antibody as primary and secondary antibodies, staining methods employing gold colloid, agglutination method, latex method and chemical luminescence.

Antibody fragments may also be used for FOXM1 detection of cancer treatment. Antibody fragments can be obtained, for example, by enzymatic means by eliminating the Fc part of the antibody with enzymes such as papain or pepsin, by chemical oxidation or by genetic manipulation of the antibody genes. It is also possible and advantageous to use genetically manipulated, non-truncated fragments. These antibodies or fragments thereof can be used alone or in mixtures.

In one embodiment, the agent that decreases the expression of FOXM1 is a nucleic acid. Exemplary nucleic acids include, but are not limited to, a deoxyribonucleic acid or a ribonucleic acid. In one embodiment, the ribonucleic acid has a nucleotide sequence that is complementary to a portion of the nucleotide sequence encoding FOXM1.

In another embodiment, RNA interference may be used as an inhibitor of FOXM1 expression. RNA interference relates to sequence-specific, posttranscriptional gene silencing brought about by double-stranded RNA that is homologous to the silenced gene target. Methods for inhibiting production of a protein utilizing small interfering RNAs are well known to the art, and disclosed in, for example, PCT Publication Numbers WO 01/75164; WO 00/63364; WO 01/92513; WO 00/44895; and WO 99/32619. RNA interference constructs or siRNA duplex RNA molecules can be used to interfere with expression of FOXM1. Typically at least 19, 21, 22, or 23 nucleotides of FOXM1 are sufficient for a siRNA molecule. Preferably a siRNA molecule will have a 2-nucleotide 3' overhang. If the siRNA is expressed in a cell from a construct, for example, from a hairpin molecule or from an inverted repeat of the desired FOXM1 sequence, then the endogenous cellular machinery will create the overhangs. The siRNA molecules can also be prepared by chemical synthesis, in vitro transcription, or digestion of long dsRNA by Rnase III or Dicer. Brummelkamp, et al., *Science,* 296:550-53 (2002); Elbashir, et al., *Nature,* 411:494-98 (2001); Elbashir, et al., *Genes Dev,* 15:188-200 (2001).

In another aspect, the invention provides a method of modulating the activity or expression of FOXM1. Such methods include administering a composition comprising an agent that modulates an activity of FOXM1, such as a protein activity or protein or RNA level of FOXM1. In one embodiment, this method comprises administering a therapeutic amount of an agent. In some embodiments, the agent decreases the activity or expression of FOXM1. In another embodiment, this comprises administering a therapeutic amount of an agent that increases the activity or expression of FOXM1. In additional embodiments, the agent can be any agent described herein or discovered by the methods described herein. By way of nonlimiting an example, an agent may bind to and interacts with FOXM1, a FOXM1 inhibitor, or a FOXM1 activator. In some embodiments, the agent may modify FOXM1 transcription, FOXM1 translation, or the FOXM1 signal pathway. In some embodiments, the methods are used to modulate FOXM1 in lung, colon, or breast cells.

In another aspect, the invention provides a pharmaceutical composition comprising an agent that modulates FOXM1 and a pharmaceutically acceptable carrier. The pharmaceutical composition can be used for treating cancer. Nonlimiting examples of cancer that can be treated by this method include lung, colon, and breast cancer. The agent may be any of the agents described herein or discovered by methods described herein. In some embodiments, the agent decreases the activity or expression of FOXM1. In some embodiments, the agent interacts directly with the protein, DNA, or RNA of FOXM1. In additional embodiments, the agent interacts with an inhibitor of FOXM1 activity or expression. In still other embodiments, the agent interacts with an activator of FOXM1 activity or expression.

The agent may be administered by a wide variety of routes. Exemplary routes of administration include oral, parenteral, transdermal, and pulmonary administration. For example, the agents may be administered intranasally, intramuscularly, subcutaneously, intraperitonealy, intravaginally and any combination thereof. For pulmonary administration, nebulizers, inhalers or aerosol dispensers may be used to deliver the therapeutic agent in an appropriate formulation (e.g., with an aerolizing agent). In addition, the agent may be administered alone or in combination with other agents, known drugs, or treatment methods. In combination, agents may be administered simultaneously or each agent may be administered at different times. When combined with one or more known anti-cancer drugs, agents and drugs may be administered simultaneously or the agent can be administered before or after the drug(s).

In one embodiment, the agents are administered in a pharmaceutically acceptable carrier. Any suitable carrier known in the art may be used. Carriers that efficiently solubilize the agents are preferred. Carriers include, but are not limited to a solid, liquid or a mixture of a solid and a liquid. The carriers may take the form of capsules, tablets, pills, powders, lozenges, suspensions, emulsions or syrups. The carriers may include substances that act as flavoring agents, lubricants, solubilizers, suspending agents, binders, stabilizers, tablet disintegrating agents and encapsulating materials.

Tablets for systemic oral administration may include excipients, as known in the art, such as calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with disintegrating agents, such as maize, starch or alginic acid, binding agents, such as gelatin, collagen or acacia and lubricating agents, such as magnesium stearate, stearic acid or talc.

In powders, the carrier is a finely divided solid, which is mixed with an effective amount of a finely divided agent.

In solutions, suspensions, emulsions or syrups, an effective amount of the agent is dissolved or suspended in a carrier such as sterile water or an organic solvent, such as aqueous propylene glycol. Other compositions can be made by dispersing the inhibitor in an aqueous starch or sodium carboxymethyl cellulose solution or a suitable oil known to the art.

The agents are administered in a therapeutic amount. Such an amount is effective in treating cancer. This amount may vary, depending on the activity of the agent utilized, the location and stage of the cancer, and the health of the patient. The term "therapeutically effective amount" is used to denote treatments at dosages effective to achieve the therapeutic result sought. Furthermore, a skilled practitioner will appreciate that the therapeutically effective amount of the agent may be lowered or increased by fine-tuning and/or by administering more than one agent, or by administering an agent with another compound. As illustrated in the following examples, therapeutically effective amounts may be easily determined, for example, empirically by starting at relatively low amounts and by step-wise increments with concurrent evaluation of beneficial effect. (e.g., reduction in symptoms).

When one or more agents or anti-cancer compounds are combined with a carrier, they may be present in an amount of about 1 weight percent to about 99 weight percent, the remainder being composed of the pharmaceutically acceptable carrier.

The invention also provides for kits that can be used for screening tissue to determine if a subject, including but not limited to a patient, has or is at risk of developing cancer. Such kits can include one or more of the following: at least one container for a tissue sample, at least one component for detection of FOXM1 (including but not limited to an antibody of FOXM1), at least one component for quantification or visualization of the level of FOXM1, at least one container for mixing the above components either alone or with a sample tissue, a control level for comparison, and a control sample to determine whether the screening method is working properly. Such a kit may also include instructions directing the use of these materials. In another embodiment, a kit may include an agent used to treat cancer with or without such above-mentioned materials that may be present to determine if a subject has or is at risk of developing cancer.

Reference will now be made to specific examples illustrating the invention. It is to be understood that the examples are provided to illustrate preferred embodiments and that no limitation to the scope of the invention is intended thereby.

EXAMPLE 1

Determination of Differential Gene Expression of FOXM1

To determine genes differentially expressed in various cancer and normal tissues, expression profiling data from primary human cancer samples were obtained from the Gene Logic® BioExpress® Database (Gaithersburg, Md.). Thirty-two samples from normal lung tissues, nineteen samples from lung cancer tissues, thirty-four samples from normal colon tissues, twenty-five samples from colon cancer tissue, twenty-five samples from normal breast tissues, and thirty-eight samples from breast cancer tissues were compared on Affymetrix® HgU95Av2 gene chips (Santa Clara, Calif.), and analyzed using Affymetrix® GeneChip® analysis software.

Additionally, isolated RNAs from each tissue sample were hybridized to Affymetrix® HGU95A chips. The RNAs hybridized to the chips were scanned on a a Hewlett-Packard® GeneArray Scanner, Model G2500A (Palo Alto, Calif.). Analyses of the data from the scans were performed using GeneChip® 3.1 program (Affymetrix, Santa Clara, Calif.) and GeneSpring® (Silicon Genetics, Redwood, CA). Initial data processing was performed using the GeneChip 3.1 program, and gene frequencies were determined using the Wyeth proprietary bacterial RNAs spiked-in at different levels to provide a standard curve. Further details on these methods are disclosed in Lockart, et al., *Nat. Biotechnol.*, 14:1675-80 (1996) and Hill, et al., *Genome Biol.*, 2:RESEARCH 0055 (2001).

Three groups of analyses were performed by comparing the cancer tissue samples to corresponding normal tissues. For these comparisons, the difference average for qualifier 34715 at FOXM1 was used to calculate the average expression value in each tissue. As shown in FIG. 1, the three groups of comparisons include: (i) all normal lung tissue samples (32) compared to the lung cancer samples (19); (ii) all normal colon tissue samples (34) compared to the colon cancer samples (25); and (iii) all normal breast tissue samples (25) compared to the breast cancer samples (38). The number of samples in each sample set is indicated above each bar. As FIG. 1 shows, mRNA levels of FOXM1 were strongly increased in all cancer samples.

EXAMPLE 2

The FOXM1 Transcript is Significantly Increased in Primary Infiltrating Ductal Carcinomas Primary tissue expression profiling data. Expression profiling data from primary human cancer samples was obtained from the Gene Logic® BioExpress® Database (Gaithersburg, Md.). Infiltrating ductal carcinoma samples (n=194) were chosen at random from the database. Normal samples (n=14) were taken from patients undergoing reduction mammoplasty. Data from patients with fibrocystic breast disease (n=10) and fibroadenoma (n=7) were filtered to remove patients with concomitant malignant disease elsewhere in the breast at the time of surgery. RNA from each sample was analyzed on Affymetrix® HgU95A chips and normalized with MAS 4.0. Difference averages for qualifier 34715 at were used for statistical analysis, and negative difference averages were assigned a value of 1. P values were calculated using the Mann-Whitney U-test.

Taqman® analysis. Breast cancer and adjacent normal tissue samples, with accompanying clinical data, were obtained from Genomics Collaborative (Cambridge, Mass.). RNA was isolated from stage II and III infiltrating ductal carcinomas as well as adjacent normal tissue from each patient. Real-time PCR was performed using the forward primer 5' GACAGGT-TAAGGTTGAGGAGCCT-3' (SEQ ID NO: 1), reverse primer 5' GTGCTGTTGATGGCGAATTGT-3' (SEQ ID NO: 2), and FAM-labeled probe 5' TGTCTGAGCGGCCAC-CCTACTCTTACA-3' (SEQ ID NO: 3). Taqman® one-step RT-PCR Master Mix Reagents (Applied Biosystems®) were used for reverse transcription and real-time PCR according to the manufacturer's instructions. The pre-developed assay reagent Human ribosomal protein PG (Applied Biosystems, Foster City, Calif.) was used as a control for normalizing FOXM1 expression. Relative amounts of transcript were determined by generating a standard curve with human Universal Reference RNA (BD Clontech®). Reactions were performed in triplicate and the average and standard deviation are shown. Fold change represents the ratio of FOXM1 in cancer tissue as compared to the adjacent normal tissue.

Cell Culture: human breast tumor cell lines MCF-10A and MCF-12A, representing non-transformed breast epithelial cells, and five breast cancer cell lines (MCF-7, BT-474, SK-BR-3, BT-20, and MDA-468) were obtained from American Type Culture Collection® (ATCC®) (Manassas, Va.). All cells were cultured according to ATCC®'s instructions.

Immunoblot analysis of FOXM1 protein levels: culture cells were lysed in buffer containing 10mM Tris buffer, pH 7.4, 1% SDS, 1 mM sodium orthovanadate, and complete protease inhibitors (F. Hoffmann-La Roche Ltd, Basel, Switzerland). Protein concentrations were analyzed using the BCA assay (Pierce, Woburn, MA), and equivalent amounts of protein were loaded on 12% SDS-PAGE gels. Proteins were transferred to Optitran® nitrocellulose (Schleicher and Schuell, Keene, N. H.) and blotted with antibodies against FOXM1 (MPP2 K-19, Santa Cruz Biotechnology, Inc., Santa Cruz, CA) or β actin (A-5441, Sigma Chemical Co., St. Louis, Mo.).

Figure 2:
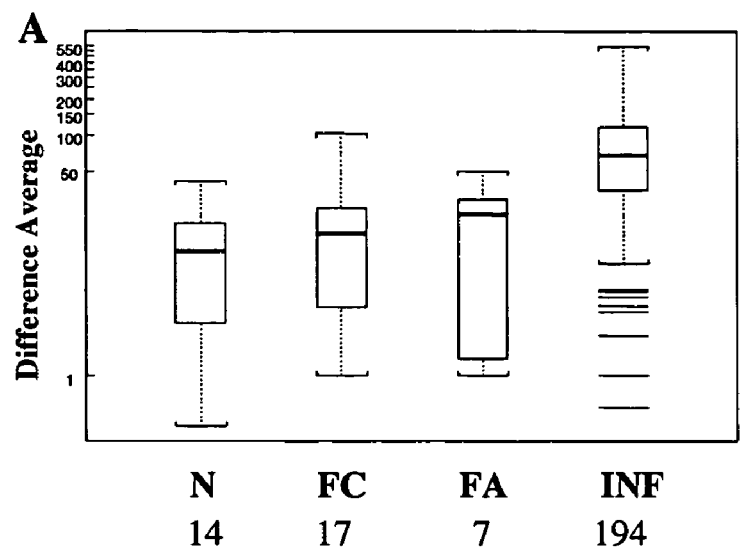
FIGS. 2A-2C.
Figure 2:
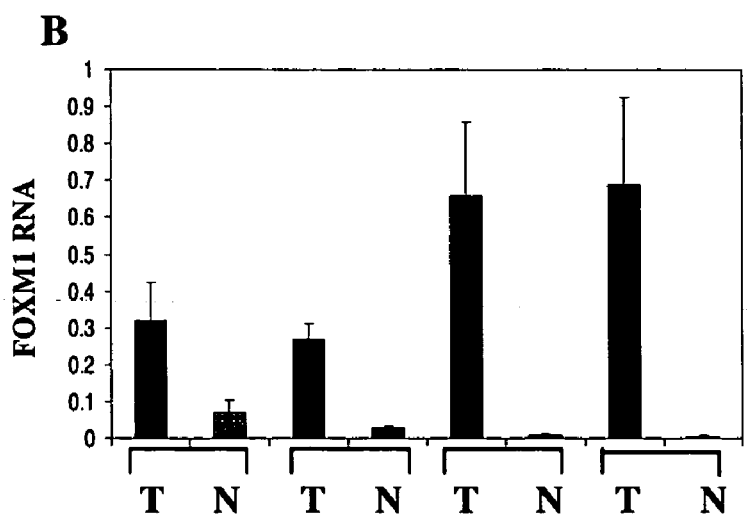
Figure 2:
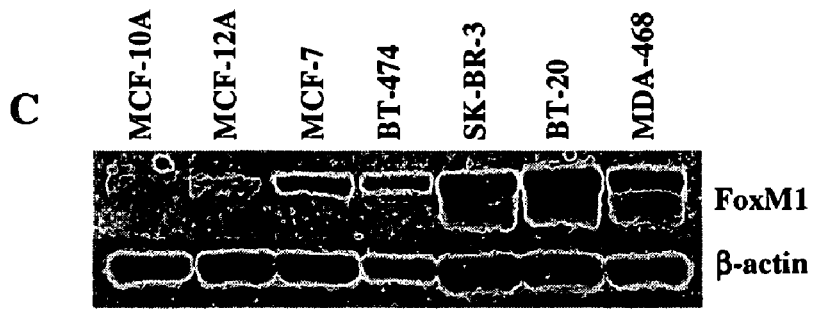

Affymetrix® HgU95A data were analyzed from 194 infiltrating ductal carcinomas present in the Gene Logic® tissue database. Tissue from reduction mammoplasty was used as a control for normal breast tissue. Comparison of ductal carcinoma and normal breast tissue identified a transcript, FOXM1, which was increased relative to normal tissue (FIG. 2A). The FOXM1 transcript was significantly elevated in breast cancer (IDC) relative to normal breast tissue (N) (Mann-Whitney U test p value=1.6E-8), fibrocystic breast disease (FC) (p=6.0E-8), and fibroadenomas (FA) (p=0.0012), indicating that FOXM1 is specifically increased in infiltrating ductal carcinomas but not in benign breast disorders.

In order to confirm the microarray data, Taqman® analysis was performed on matched tissue samples from stage II and III ductal carcinomas (T) and adjacent normal tissue (N) (FIG. 2B). RNA was isolated from stage II and III infiltrating ductal carcinomas as well as adjacent normal tissue from each patient. Taqman® analysis was performed using primers listed above that are specific to FOXM1 or the ribosomal protein 36B4 as a control. Relative amounts of transcript were determined by generating a standard curve with human Universal Reference RNA (BD Biosciences Clontech, Palo Alto, Calif.). Reactions were performed in triplicate and the average and standard deviation are shown in FIG. 2B. As FIG. 2B shows, FOXM1 RNA level increases in the carcinomas cells compared to normal tissue cells adjacent to the carcinomas for all of the four patients tested. Fold change represents the ratio of FOXM1 in cancer tissue as compared to the adjacent normal tissue. Stage II carcinomas showed an increase of four and nice fold relative to adjacent normal tissue, while the two stage III carcinomas showed an increase of 76 and 116-fold.

FIG. 2C demonstrates that FOXM1 protein is also overexpressed in breast cancer cell lines. Western blotting of the MCF-10A and MCF-12A normal mammary epithelial cell lines as well as five transformed breast epithelial cell lines (MCF-7, BT-474, SK-BR-3, BT-20, and MDA-468) indicates that FOXM1 protein is also increased in breast cancer cell lines.

These results indicate that FOXM1 expression is increased in primary infiltrating ductal carcinoma and the increase is significant relative to both normal tissue and benign breast disease. In addition, the FOXM1 protein is consistently overexpressed in breast cancer cell lines. Furthermore, Taqman® analysis of matched pairs of tumor tissue and adjacent normal tissue confirms the micro array data and indicates that although there is a wide range of expression differences, from 4-fold to 116-fold, FOXM1 expression is elevated relative to adjacent normal tissue in all samples examined by real-time PCR.

EXAMPLE 3

Suppression of Cell Growth with FOXM1 siRNA

Cell Culture: human breast tumor cell lines BT-20 and MCF-7 were obtained from American Type Culture Collection® (ATCC®) (Manassas, Va.). BT-20 cells were maintained in Eagle's Minimum Essential medium with 10% Fetal Bovine Serum (FBS). MCF-7 cells were cultured in Dulbecco's Modified Eagle's Medium with 10% FBS.

Cell Proliferation Assays. The cell proliferation reagent WST-1 (F. Hoffmann-La Roche Ltd.), which measures cleavage of the tetrazolium salt WST-1 by mitochondrial dehydrogenases, was used to assay cell number. Cells were trypsinized 24 hours after transfection and plated in 96-well plates. Absorbance at 450 nm was assayed 2 hours after adding WST-1.

RNAi. Annealed, purified, double-stranded oligonucleotides were obtained from Dharmacon (Lafayette, Colo.). The FOXM1 siRNA sequence was CCUUUCCCUGCAC-GACAUGdTdT (SEQ ID NO: 4). The GFP control oligo sequence was CAAGCUGACCCUGAAGUUCdTdT (SEQ ID NO: 5). For transfections, cells were plated at approximately 50% confluence and transfected with 200 nM oligo using siPORT, Ambion® (Austin, Tex.), for 5 hours according to the manufacturer's instructions. Stable expression of the FOXM1 shRNA was achieved using the pSilencer 3.1 H1 puro vector (Ambion®), with a FOXM1 hairpin sequence based on the FOXM1 siRNA indicated above, according to the manufacturer's instructions for hairpin design. The negative control vector is the pSilencer 3.1 H1 puro vector containing a 66 base pair hairpin with limited homology to known sequences in the human genome, supplied by the manufacturer (Ambion®).

Treatment of cells with FOXM1 siRNA: BT-20 or MCF-7 cells were incubated for five hours with lipid reagent alone (mock), siRNA to green fluorescent protein (GFP), or siRNA targeting FOXM1 (FM931 for BT-20; FM606 for MCF-7). Cells were collected at the indicated timepoints and analyzed either by Western blot for FOXM1 protein levels or by Taqman® analysis for FOXM1 RNA levels.

Figure 3:
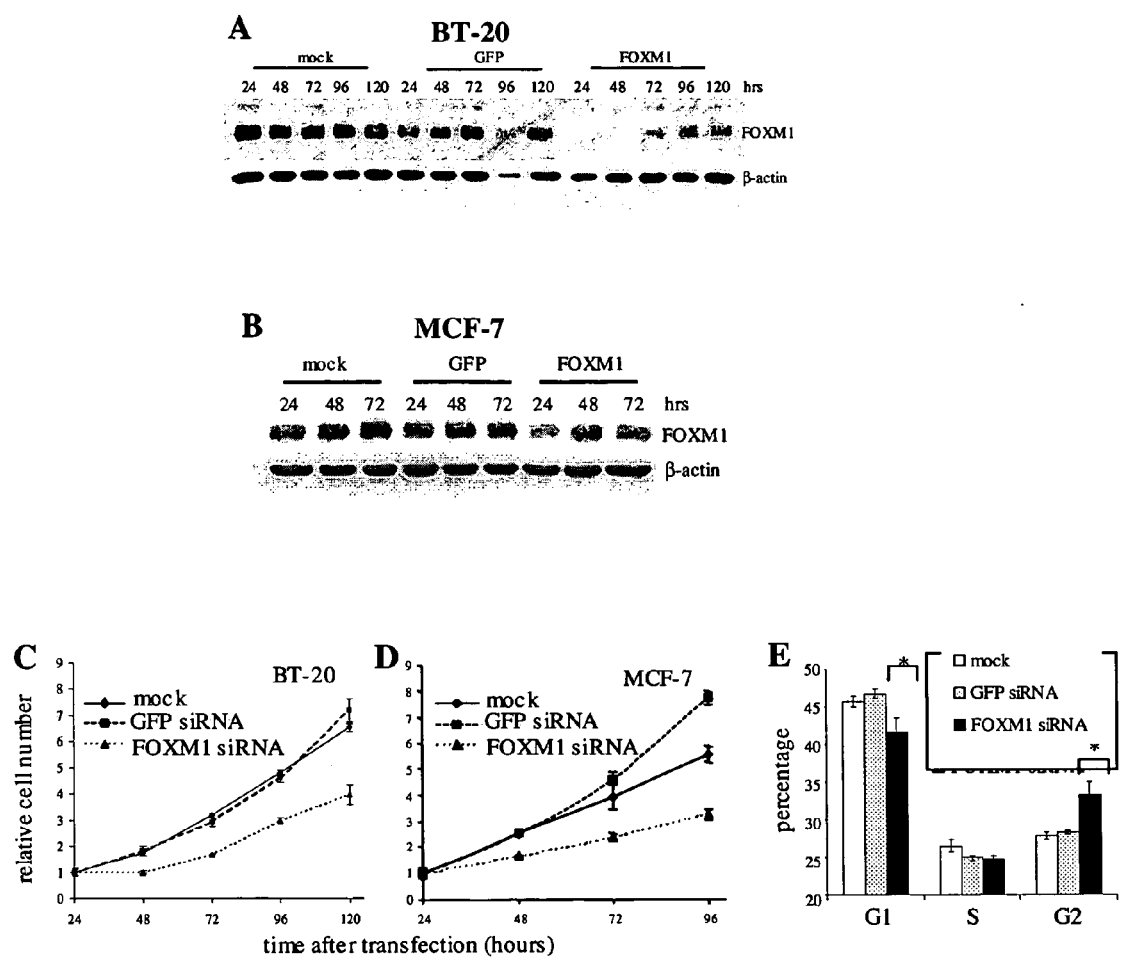
FIGS. 3A-3B.
FIG. 3C is a graphic representation of the growth curve of BT-20 cells after FOXM1 siRNA treatment.
FIG. 3D is a graphic representation of the growth curve of MCF-7 cells after FOXM1 siRNA treatment.
FIG. 3E is graphic representation of the percentage of BT-20 cells in each phase of the cell cycle after FOXM1 siRNA treatment.

FIGS. 3A-3B show FOXM1 protein expressions at different timepoints after treatment of BT-20 and MCF-7 cells with FOXM1 siRNA. The cells were incubated for 5 hours with lipid reagent alone (mock), siRNA to green fluorescent protein (GFP), or siRNA targeting FOXM1. Cells were collected at the indicated timepoints and analyzed by Western blot using FOXM1 specific antibody or β-actin as a loading control. As FIGS. 3A-3B shows, the treatment with FOXM1 siRNA reduced FOXM1 protein expression 24 hours after the treatment. In comparison, FOXM1 protein levels were not affected by treatment with the mock or the GFP control. Timepoints taken 24, 48, and 72 hours after transfection indicate that FOXM1 siRNA effectively reduced expression of the FOXM1 protein, while mock-transfected and GFP oligo-transfected cells did not show a decrease in FOXM1.

The phenotype of BT-20 and MCF-7 breast cancer cells was then examined with reduced FOXM1 expression. Cells were plated 24 hours after transfection and analyzed using WST-1, which measures mitochondrial dehydrogenase activity and reflects cell number. Both cell lines displayed a decrease in proliferation over the time course examined (FIGS. 3C-3D). BT-20 cells showed a maximal growth inhibition of 46% at 72 hours post-transfection, while MCF-7 cells were inhibited 39% relative to mock-transfected cells. Another siRNA targeting FOXM1 was also used and showed similar growth inhibition in both cell lines (data not shown).

Analysis of BT-20 cells at 48 hours post-transfection indicated an increase in the percentage of cells in G2/M and a concomitant decrease in the G1 population (FIG. 3E). Therefore, FOXM1 siRNA induces a block in the cell cycle, which is sufficient to alter the proliferation of BT-20 and MCF-7 cells.

EXAMPLE 4

Stable FOXM1 shRNA Decreases Cell Viability

Crystal Violet Staining. Following transfection, $2.5 \times 10^5$ cells per well were plated in 6-well dishes. At the indicated times, cells were fixed in 0.5% glutaraldehyde, washed, and stained with 0.2% crystal violet.

Cell transfection with shRNA. BT-20 cells were transfected with Effectene® transfection reagent (Qiagen, Valencia, Calif.) according to the manufacturer's instructions and a control shRNA (Ambion®).) or a stable construct expressing FOXM1 shRNA:

(SEQ. ID. NO:6)
5' GATCGCCTTT CCCTGCACGA CATGATCTCG AGGCATGTCG TGC

AGGGAAA GGTTTTTTGG AAC 3'

CGGAAA GGGACGTGCT GTACTAGAGC TCCGTACAGC ACGTCCCTTT

CCAAAAAACC TTGTCGA.

Transfected cells were selected for 6 days in the presence of 0.5 mg/mL puromycin.

Figure 4:
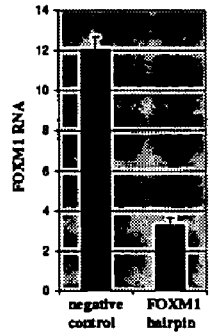
FIGS. 4A-4B.
FIG. 4C is a photographic representation of cell survival after treatment with control shRNA or FOXM1 shRNA and crystal violet staining.
Figure 4:
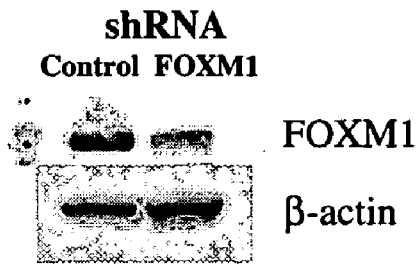
Figure 4:
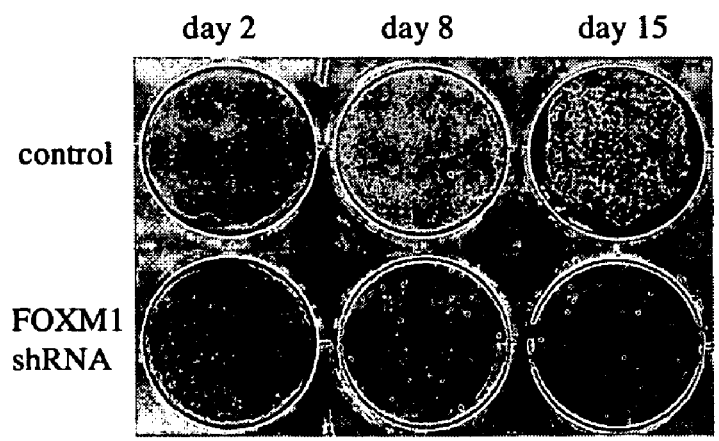
Figure 5:
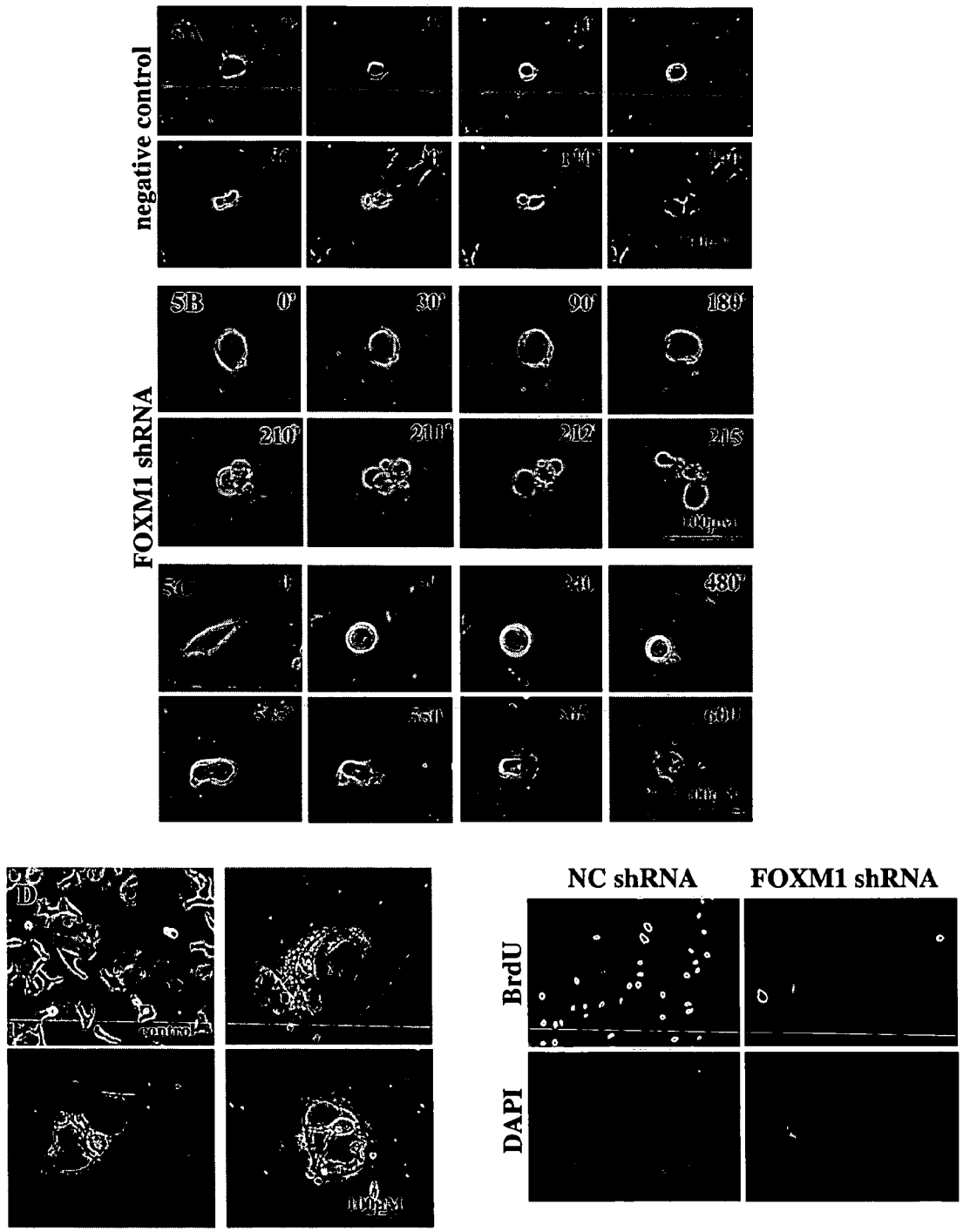
FIGS. 5A-5E.

In order to evaluate the consequences of continuous depletion of FOXM1, BT-20 cells were transfected with control shRNA or FOXM1 shRNA. Cell viability was then evaluated with crystal violet staining. FIG. 4A demonstrates the experimental timeline for FIGS. 4-9. FIG. 4B demonstrates that the FOXM1 shRNA construct was effective in reducing both FOXM1 RNA and protein expression after six days in selection media. FIG. 4C demonstrates that although cells were plated at the same density prior to selection (day 2), following selection for six days there were fewer FOXM1 shRNA cells surviving as compared to control cells (day 8). After additional seven days of growth, control cells continued to proliferate, while the number FOXM1 shRNA cells continued to decrease (day 15). These results indicate that disruption of FOXM1 affects cell survival and inhibits the outgrowth of cells with reduced FOXM1.

EXAMPLE 5

Mitotic Catastrophe and Polyploidy is Induced in FOXM1 shRNA Cells

Timelapse imaging. Cells in 6-well dishes were placed in CO2 independent Gibco® medium (Invitrogen, Carlsbad, Calif.), overlaid with mineral oil, and maintained at 37° C. Images were captured at regular intervals using an Olympus® inverted microscope equipped with a Zeiss® AxioCam® HRC digital imaging system.

BrdU Assay. Cells were labeled for 20 hours with BrdU (5-bromo-2'-deoxyuridine) and analyzed with the BrdU Labeling and Detection Kit (Roche Applied Science, Indianapolis, Ind.) according to the manufacturer's instructions. Cells were examined by fluorescence microscopy and scored for BrdU staining. The percentage of BrdU-positive cells was obtained from at least 200 nuclei for each sample.

Immunohistochemistry. Cells were plated on glass coverslips coated with poly-D-lysine and allowed to adhere overnight. For analysis of α tubulin, cells were fixed in 3% paraformaldehyde/PBS for 20 minutes, washed in PBS, and permeabilized with 0.5% Triton-X-100 for 3 minutes. Blocking was performed with 5% BSA in PBS for 6 hours. Monoclonal α tubulin antibody (Sigma clone B-5-1-2) was diluted 1:1000 in 3% BSA/PBS, incubated overnight at 4° C., and detected with AlexaFluor® 488 goat anti-mouse IgG (Molecular Probes®). For detection of centrosomes, cells were fixed with a 1:1 mixture of acetone :methanol at −20° C. for 10 minutes and incubated with γ tubulin monoclonal antibody (clone GTU-88) from Sigma at a dilution of 1:2000. All other steps were identical to the staining for α tubulin. Cells were counterstained with DAPI (4', 6-Diamidino-2-phenylindole, dihydrochloride) before mounting with ProLong® antifade reagent (Molecular Probes, Eugene, Oreg.). Images were obtained with a Zeiss® AxioCam® HRC digital imaging system. The percentage of cells with mitotic spindle defects was determined by counting 100 mitotic cells from three different transfections for both the negative control and FOXM1 shRNA. Cells were scored as abnormal if they displayed spindles with over two poles. The percentage of cells with amplified centrosomes was determined by counting at least 200 cells from three different transfections for negative control and FOXM1 shRNA. Centrosome amplification was identified by cells with over two centrosomes.

Figure 6:
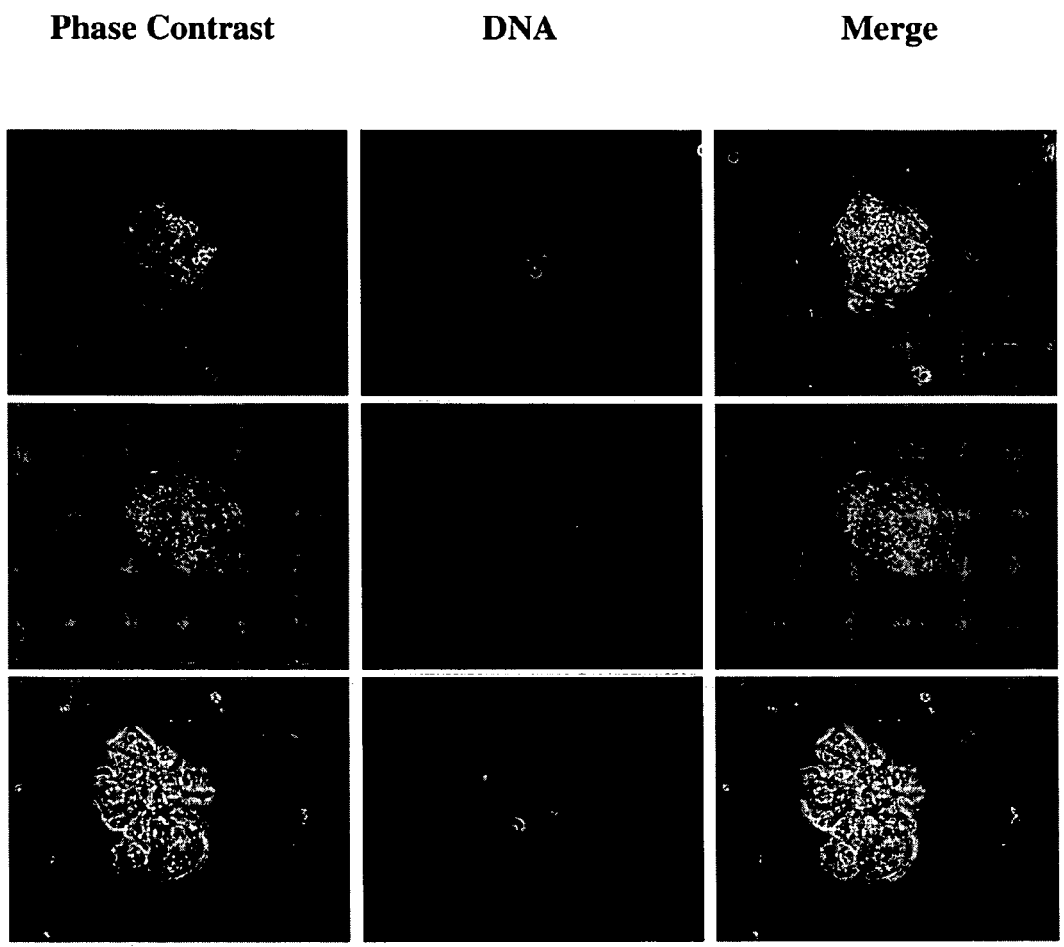
FIG. 6.
Figure 7:
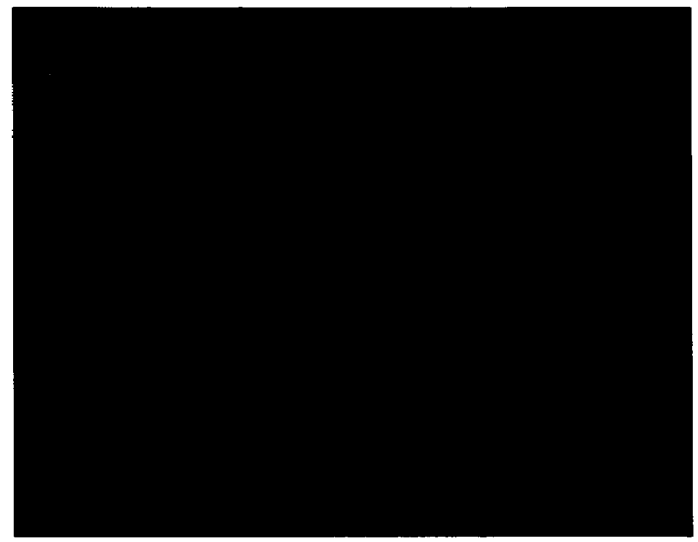
FIG. 7.
Figure 7:
Figure 8:
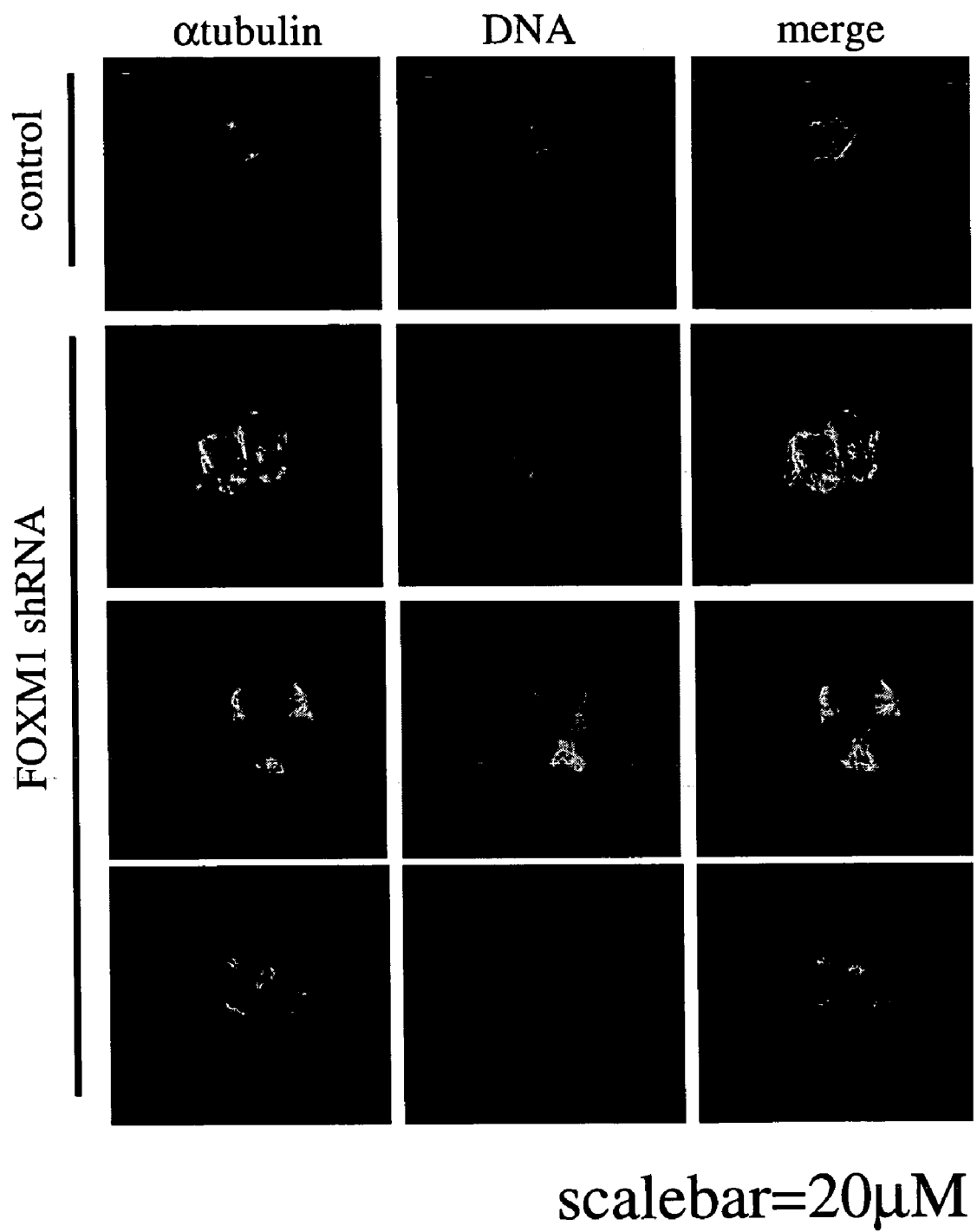
FIGS. 8A-8D.
Figure 9:
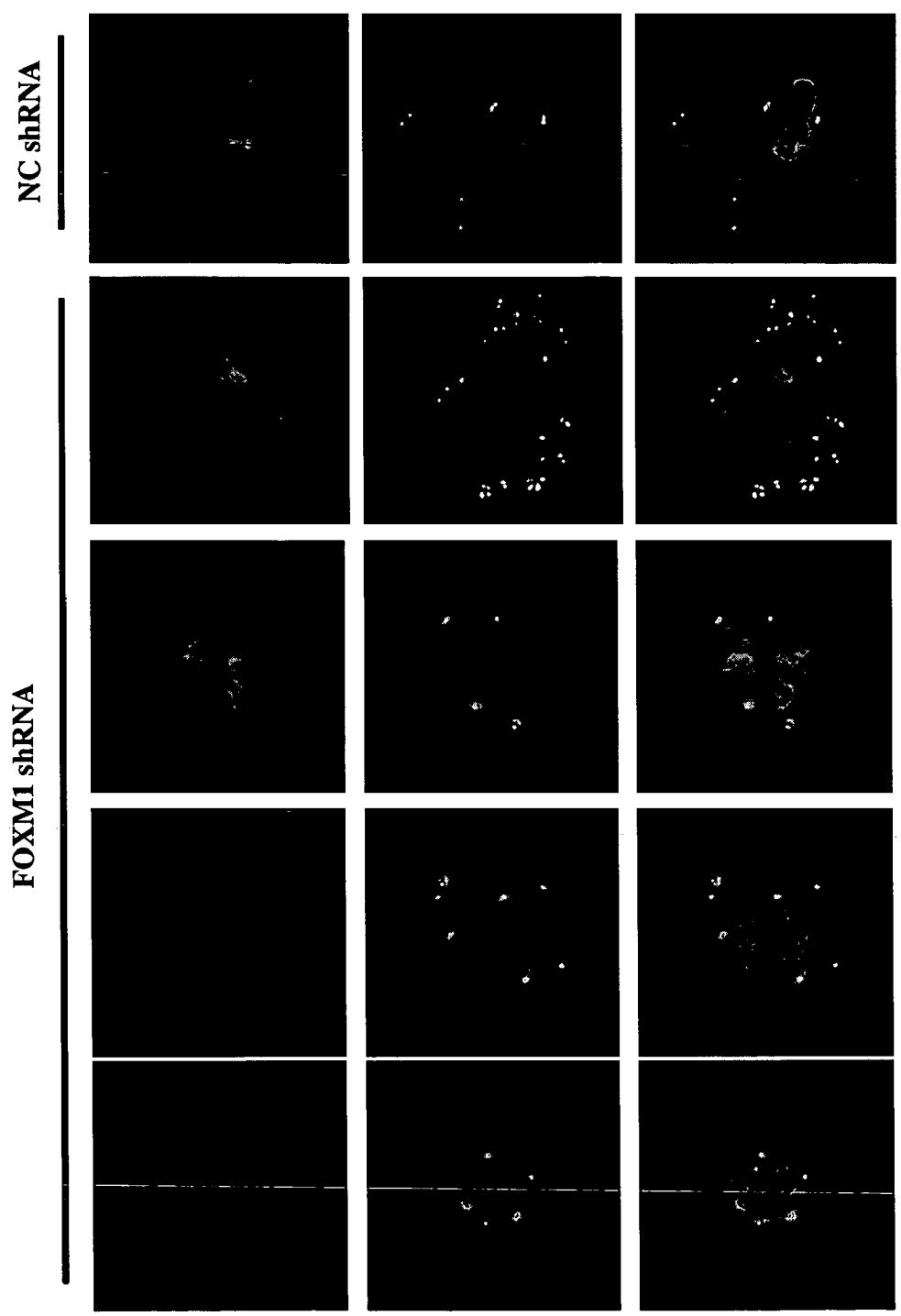
FIGS. 9A-9E.

Timelapse microscopy was used to follow cells through mitosis. FIG. 5A demonstrates that a control cell initiates mitosis, undergoes cytokinesis, and returns to interphase within 120 minutes. In contrast, it was discovered that there are two distinct outcomes for cells expressing FOXM1 shRNA. The majority of cells initiates mitosis but is unable to divide, eventually undergoing cell death while in mitosis (FIG. 5B). The morphology of these cells is identical to previously reported instances of mitotic catastrophe, including catastrophe induced by siRNA to hNuf2 (DeLuca et al., *J. Cell Biol.* 159:549-555 (2002)) or ionizing radiation (Nitta et al., *Oncogene* (2004)). In addition, DAPI staining of nuclei revealed multinucleation that is typical of mitotic catastrophe (FIG. 6). Therefore, it is concluded that most of the cells with decreased FOXM1 expression enter mitosis but are unable to divide, and cell death results from mitotic catastrophe. A smaller population of cells initiates mitosis, does not divide, and exits mitosis without completing nuclear division or cytokinesis (FIG. 5C). These cells undergo a prolonged arrest after initiating mitosis, averaging 450±150 minutes. This leads to the formation of enlarged cells with polyploid nuclei (FIG. 5E (DAPI stained cells) and FIG. 7), similar to the phenotype observed in hepatocytes and cardiomyoctes of FOXM1 knockout mice (Korver et al., *Curr. Biol.* 8:1327-1330 (1998)). This population of cells was able to undergo several rounds of DNA replication in the absence of cell division, and eventually underwent cell death (21 days after transfection), although the cells did not resemble traditional apoptotic or necrotic cells (FIG. 5D). However, the cells did resemble the enlarged, flattened morphology that is typical of senescent cells. Therefore, cells were stained for the presence of SA-β-gal activity, a well-characterized marker of senescence (Dimri et al., *Proc. Natl. Acad. Sci. U.S.A.* 92:9363-9367 (1995)). Neither control nor FOXM1 shRNA cells were positive in this assay (data not shown). However, they did show reduced incorporation of BrdU. At 21 days post-transfection, cells were labeled with BrdU for 20 hours and analyzed with a monoclonal antibody against BrdU. Negative control cells were 85% positive for BrdU, while the percentage of positive cells dropped to 40% when FOXM1 expression was reduced (FIG. 5E). Thus, although a population of FOXM1 shRNA cells is able to undergo endoreduplication, these cells eventually lose their capacity to replicate DNA and undergo cell death.

EXAMPLE 6

Depletion of FOXM1 Induces Mitotic Spindle Aberrations

In order to determine whether defective spindle formation plays a role in the mitotic failure of cells expressing FOXM1 shRNA, the mitotic spindle was examined using anti a tubulin antibodies to stain microtubules. FIG. 8A indicates a typical mitotic cell, with a bipolar spindle, transfected with control shRNA. FIGS. 8B-8D represent various mitotic abnormalities found in FOXM1 shRNA-transfected cells. FIG. 8B is a representative example of a metaphase cell that contains condensed chromatin but lacks an organized mitotic spindle, with multiple apparent spindle poles throughout the cell. FIGS. 8C and 8D indicate an organized tripolar or tetrapolar spindle, respectively, that is typically seen in cells with reduced FOXM1. Quantitative analysis of mitotic cells stained with α tubulin antibodies indicates that 17% of control cells versus 59% of FOXM1 shRNA cells exhibited mitotic spindle defects.

Because centrosomes play a critical role in bipolar spindle organization, it was investigated whether the defects in spindle formation were due to centrosomal amplification using antibodies to γ tubulin, a core component of the centrosome (Wiese and Zheng, *Curr. Opin. Struct. Biol.* 9:250-259 (1999)). FIG. 9A demonstrates that control cells contain two centrosomes during interphase, and form a typical bipolar mitotic spindle. FIG. 9B indicates that FOXM1 shRNA cells contain numerous centrosomes during interphase, which leads to the formation of multiple spindle poles in mitotic cells (FIGS. 9C, 9D and 9E). These results indicate that some centrosomes are able to nucleate microtubules while others remain unattached to the mitotic spindle (FIGS. 9C and 9D, white arrows). This explains the discovery that although a majority of cells with multiple centrosomes contains 10 or more visible centrosomes during interphase, formation of mitotic spindles with more than five poles was not discovered. Because it was discovered that untransfected BT-20 cells contain a significant number of cells with over two centrosomes, centrosome number was quantitated in cells transfected with negative control or FOXM1 shRNA. After evaluating at least 200 cells from triplicate transfections, it was discovered that the percentage of cells with over two centrosomes was 19.2±1.3% in control cells versus 63.0±4.0% in FOXM1 shRNA cells. Therefore, depletion of FOXM1 significantly increases centrosome number. These results suggest that FOXM1 shRNA cells undergo mitotic catastrophe due to the formation of multipolar spindles arising from supernumerary centrosomes.

EXAMPLE 7

Screening Assay for Genes Regulated by FOXM1

Microarray Analysis. BT-20 cells were transfected in triplicate using either a mock transfection (no siRNA), GFP siRNA, or FOXM1 siRNA. Cells were collected 48 hours after transfection, and RNA was isolated using the RNeasy® Mini Kit (Qiagen, Valencia, Calif.). Generation of labeled target for hybridization was essentially as described. Lockhart et al., *Nat. Biotechnol.* 14:1675-1680 (1996). Briefly, eight micrograms of total RNA was used to generate first-strand cDNA using a T7-oligo d(T) primer. Following second strand synthesis, in vitro transcription was performed using biotinylated CTP and UTP (Enzo diagnostics, Farmingdale, New York). Fifteen micrograms of biotinylated RNA was fragmented prior to overnight hybridization on Affymetrix® HgU133A arrays. Arrays were analyzed and absent/present calls were determined with Affymetrix® GeneChip® software. Transcript abundance was calculated by comparing the signal value of each transcript to the signal value of a cRNA spike-in standard curve. Hill et al., *Genome Biol.* 2 RESEARCH 0055 (2001). Fold change analysis was performed using the average of mock and GFP-transfected cells (n=6 total) relative to the average of FOXM1 siRNA-transfected cells (n=3). P-values were calculated using the Student's t test. Data were filtered using a fold change cutoff of ±1.70, a p value cutoff of 0.010000 or less, and at least 3 "present" calls for each probe set.

Analysis thus was performed on cells that had been transfected with FOXM1 siRNA and expression of approximately 22,000 transcripts was monitored on Affymetrix® microarrays. Using mock and GFP-transfected cells as a control, a set of genes were discovered that was uniquely regulated in cells transfected with FOXM1 siRNA (FIG. 10). These genes, thus relating to the FOXM1 signaling pathway, include those involved in transcription, such as forkhead box M1 (FOXM1), down-regulator of transcription 1 (DR1), zinc finger protein 302 (ZNF302), high-mobility group protein 17-like 3 (HMGN4), WD40 protein Ciao1 (CIAO1), and retinoblastoma binding protein 1 (RBBP1); in cell cycle and chromosome segregation, such as cyclin-dependent kinase inhibitor 3 (CDKN3), cell division cycle 25B (CDC25B), RAB6 interacting, kinesin-like (KIF20A), NIMA-related kinase 2 (NEK2), cyclin A2 (CCNA2), centromere protein A (CENPA), KIAA0699 protein (BICD2), KIAA1026 protein (KIAA1026), and dual specificity phosphatase 6 (DUSP6); and in metabolism, such as cytochrome P450, subfamily I (CYP1A1), glutathione reductase (GSR), glucosamine-6-phosphate isomerase (GNPI), and retinal short-chain dehydrogenase (RETSDR2). Genes that are involved in the FOXM1 signaling pathway also include cytokines such as epiregulin (EREG) and interleukin 8 (IL8) and other molecules such as ras homolog gene family, member D (ARHD), rabaptin-5 (RAB5EP), death-associated protein kinase 3 (DAPK3), protein tyrosine phosphatase, receptor type, G (PTPRG), monocyte to macrophage differentiation (MMD), Sjogren syndrome antigen A2 (SSA2), ribosomal protein L23 (RPL23), protein tyrosine phosphatase, non-receptor type 18 (PTPN18), hypothetical protein FLJ13949 (TOE1), tumor protein p53-binding protein (TP53BPL), coagulation factor II (thrombin) receptor-like 1 (F2RL1), hypothetical protein FLJ11753 (FLJ11753), serine (or cysteine) proteinase inhibitor (SERPINE1), and $H^+$ transporting ATPase (UNK_AW575379). All genes listed in FIG. 10 meet the criteria of at least a 1.70 fold decrease and a p-value of no larger than 0.01. Although most of the genes in FIG. 10 are down-regulated after FOXM1 siRNA treatment, RBBP1, DUSP6, EREG, IL8, AND F2RL1 were up-regulated. Among these identified genes, some are required for mitotic spindle assembly: CENP-A (a conserved variant of histone H3 and is implicated in kinetochore assembly) and NEK2 (a centrosomal kinase that is required for chromosome segregation and cytokinesis) and others are closely related to transcriptional factors and cell cycle regulators: RBBP1 (which binds Rb and recruits histone deacetylases, resulting in repression of genes regulated by E2F and inhibition of the G1/S transition) and CDKN3 (which binds and inactivates CDK2, inhibiting cell entry into S phase). These results suggest that in addition to cell-cycle regulatory genes, FOXM1 also regulates genes that are required for transcriptional control and chromosome segregation.

Genes that are regulated, directly or indirectly, by FOXM1, i.e., FOXM1 targets, are involved in the FOXM1 signaling pathway. These genes include, but are not limited to, the above listed genes. FOXM1 targets can be used to screen for specific FOXM1 inhibitors or therapeutic compounds. For example, the promoters of FOXM1 targets can be cloned upstream of a reporter gene, such as luciferase. The reporter genes can then be stably transfected into cells, and the cells are analyzed for agents, including any molecule or compound, that inhibit expression of the reporter genes. Through the use of multiple cell lines with different reporter genes, inhibitor specificity can be achieved by screening for agents that inhibit several or all of the FOXM1 targets.

EXAMPLE 8

Screening Assays for Agents Inhibiting FOXM1 Activity

FOXM1 has been shown to bind several oligonucleotide sequences (FOXM1 binding sequences) in vitro, Korver, et al., *Nucleic Acids Res.*, 25:1715-9 (1997); Yao, et al., *J. Biol. Chem.*, 272:19827-36 (1997); and Ye, et al., *Mol. Cell Biol.*, 17:1626-41 (1997). In order to screen for compounds that inhibit FOXM1 binding to DNA, a fusion protein is created containing the DNA binding domain of FOXM1 fused to the GAL4 activation domain. Another construct is made containing one or more copies of the FOXM1 binding sequences upstream of a β-galactosidase reporter construct. These two constructs are then transformed into yeast cells and analyzed for expression of β-galactosidase with a standard colorimetric assay. Compounds that inhibit the binding of FOXM1 to its target sequences would reduce expression of β-galactosidase.

EXAMPLE 9

Screening Assay for Cancer Using Determination of RNA Expression Levels of FOXM1

Samples of human normal tissue and tissue from a patient possibly having or is at risking of developing cancer are harvested after signed consent and flash frozen in liquid nitrogen. Frozen tissues are pulverized and RNA is isolated utilizing guanidinium isothiocyante and RNeasy® kit (Qiagen®). Agilent® systems are used to assess RNA quality. The levels of FOXM1 mRNA are then quantified and normalized.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method for determining whether a subject has lung, colon, or breast cancer comprising:
    (a) acquiring a first sample of tissue from the lung, colon, or breast of the subject;
    (b) measuring in the first sample the level of expression of mRNA encoding a polypeptide comprising the amino acid sequence of SEQ ID NO: 8;
    (c) measuring in a second sample of adjacent non-cancerous tissue of the same type as the first sample the level of expression of mRNA encoding the polypeptide; and
    (d) determining that the subject has lung, colon, or breast cancer if the level of expression of the mRNA encoding the polypeptide in the first sample is greater than the level of expression of the mRNA encoding the polypeptide in the second sample.

2. The method of claim 1, wherein the subject is a human.

3. The method of claim 2, wherein the first and second samples are samples of breast tissue and the cancer is breast cancer.

4. The method of claim 2, wherein the first and second samples are samples of lung tissue and the cancer is lung cancer.

5. The method of claim 2, wherein the first and second samples are samples of colon tissue and the cancer is colon cancer.

6. The method of claim 2, wherein further comprising measuring the level of the polypeptide in the first and/or second samples.

* * * * *

SEQUENCE LISTING

<160> NUMBER OF SEQ ID NOS: 9

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacaggttaa ggttgaggag cct                                              23

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgctgttga tggcgaattg t                                                21

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tgtctgagcg gccaccctac tcttaca                                          27

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
ccuuucccug cacgacaugt t                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
caagcugacc cugaaguuct t                                                21

<210> SEQ ID NO 6
<211> LENGTH: 63
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 6
gatcgccttt ccctgcacga catgatctcg aggcatgtcg tgcagggaaa ggttttttgg     60
aac                                                                   63

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agctgttcca aaaacctttc cctgcacga catgcctcga gatcatgtcg tgcagggaaa     60
ggc                                                                   63

<210> SEQ ID NO 8
<211> LENGTH: 748
<212> TYPE: PRT
<213> ORGANISM: Homo sapiens

<400> SEQUENCE: 8
```

Met Lys Thr Ser Pro Arg Arg Pro Leu Ile Leu Lys Arg Arg Leu
1               5                   10                  15

Pro Leu Pro Val Gln Asn Ala Pro Ser Glu Thr Ser Glu Glu Pro
                20                  25                  30

Lys Arg Ser Pro Ala Gln Gln Glu Ser Asn Gln Ala Glu Ala Ser
            35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

-continued

```
Tyr Met Ala Met Ile Gln Phe Ala Ile Asn Ser Thr Glu Arg Lys Arg
                245                 250                 255
Met Thr Leu Lys Asp Ile Tyr Thr Trp Ile Glu Asp His Phe Pro Tyr
            260                 265                 270
Phe Lys His Ile Ala Lys Pro Gly Trp Lys Asn Ser Ile Arg His Asn
        275                 280                 285
Leu Ser Leu His Asp Met Phe Val Arg Glu Thr Ser Ala Asn Gly Lys
    290                 295                 300
Val Ser Phe Trp Thr Ile His Pro Ser Ala Asn Arg Tyr Leu Thr Leu
305                 310                 315                 320
Asp Gln Val Phe Lys Gln Lys Arg Pro Asn Pro Glu Leu Arg Arg
                325                 330                 335
Asn Met Thr Ile Lys Thr Glu Leu Pro Leu Gly Ala Arg Arg Lys Met
            340                 345                 350
Lys Pro Leu Leu Pro Arg Val Ser Ser Tyr Leu Val Pro Ile Gln Phe
        355                 360                 365
Pro Val Asn Gln Ser Leu Val Leu Gln Pro Ser Val Lys Val Pro Leu
    370                 375                 380
Pro Leu Ala Ala Ser Leu Met Ser Ser Glu Leu Ala Arg His Ser Lys
385                 390                 395                 400
Arg Val Arg Ile Ala Pro Lys Val Leu Leu Ala Glu Glu Gly Ile Ala
                405                 410                 415
Pro Leu Ser Ser Ala Gly Pro Gly Lys Glu Glu Lys Leu Leu Phe Gly
            420                 425                 430
Glu Gly Phe Ser Pro Leu Leu Pro Val Gln Thr Ile Lys Glu Glu Glu
        435                 440                 445
Ile Gln Pro Gly Glu Glu Met Pro His Leu Ala Arg Pro Ile Lys Val
    450                 455                 460
Glu Ser Pro Pro Leu Glu Glu Trp Pro Ser Pro Ala Pro Ser Phe Lys
465                 470                 475                 480
Glu Glu Ser Ser His Ser Trp Glu Asp Ser Ser Gln Ser Pro Thr Pro
                485                 490                 495
Arg Pro Lys Lys Ser Tyr Ser Gly Leu Arg Ser Pro Thr Arg Cys Val
            500                 505                 510
Ser Glu Met Leu Val Ile Gln His Arg Glu Arg Arg Glu Arg Ser Arg
        515                 520                 525
Ser Arg Arg Lys Gln His Leu Leu Pro Pro Cys Val Asp Glu Pro Glu
    530                 535                 540
Leu Leu Phe Ser Glu Gly Pro Ser Thr Ser Arg Trp Ala Ala Glu Leu
545                 550                 555                 560
Pro Phe Pro Ala Asp Ser Ser Asp Pro Ala Ser Gln Leu Ser Tyr Ser
                565                 570                 575
Gln Glu Val Gly Gly Pro Phe Lys Thr Pro Ile Lys Glu Thr Leu Pro
            580                 585                 590
Ile Ser Ser Thr Pro Ser Lys Ser Val Leu Pro Arg Thr Pro Glu Ser
        595                 600                 605
Trp Arg Leu Thr Pro Pro Ala Lys Val Gly Gly Leu Asp Phe Ser Pro
    610                 615                 620
Val Gln Thr Ser Gln Gly Ala Ser Asp Pro Leu Pro Asp Pro Leu Gly
625                 630                 635                 640
Leu Met Asp Leu Ser Thr Thr Pro Leu Gln Ser Ala Pro Pro Leu Glu
                645                 650                 655
Ser Pro Gln Arg Leu Leu Ser Ser Glu Pro Leu Asp Leu Ile Ser Val
```

-continued

```
                660                 665                 670
Pro Phe Gly Asn Ser Ser Pro Ser Asp Ile Asp Val Pro Lys Pro Gly
            675                 680                 685

Ser Pro Glu Pro Gln Val Ser Gly Leu Ala Ala Asn Arg Ser Leu Thr
        690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
            740                 745

<210> SEQ ID NO 9
<211> LENGTH: 3326
<212> TYPE: DNA
<213> ORGANISM: Homo sapiens

<400> SEQUENCE: 9
ggagcccgga gcccgccttc ggagctacgg cctaacggcg gcggcgactg cagtctggag      60
ggtccacact tgtgattctc aatggagagt gaaaacgcag attcataatg aaaactagcc     120
cccgtcggcc actgattctc aaaagacgga ggctgcccct tcctgttcaa atgccccaa      180
gtgaaacatc agaggaggaa cctaagagat cccctgccca acaggagtct aatcaagcag     240
aggcctccaa ggaagtggca gagtccaact cttgcaagtt tccagctggg atcaagatta     300
ttaaccaccc caccatgccc aacacgcaag tagtggccat ccccaacaat gctaatattc     360
acagcatcat cacagcactg actgccaagg aaaagagag tggcagtagt gggcccaaca     420
aattcatcct catcagctgt gggggagccc caactcagcc tccaggactc cggcctcaaa     480
cccaaaccag ctatgatgcc aaaaggacag aagtgaccct ggagaccttg ggaccaaaac     540
ctgcagctag ggatgtgaat cttcctagac cacctggagc cctttgcgag cagaaacggg     600
agacctgtgc agatggtgag gcagcaggct gcactatcaa caatagccta tccaacatcc     660
agtggcttcg aaagatgagt tctgatggac tgggctcccg cagcatcaag caagagatgg     720
aggaaaagga gaattgtcac ctggagcagc acaggttaa ggttgaggag ccttcgagac     780
catcagcgtc ctgcagaac tctgtgtctg agcggccacc ctactcttac atggccatga     840
tacaattcgc catcaacagc actgagagga gcgcatgac tttgaaagac atctatacgt     900
ggattgagga ccactttccc tactttaagc acattgccaa gccaggctgg aagaactcca     960
tccgccacaa cctttccctg cacgacatgt ttgtccggga gacgtctgcc aatggcaagg    1020
tctccttctg gaccattcac cccagtgcca accgctactt gacattggac caggtgttta    1080
agcagcagaa acgaccgaat ccagagctcc gccggaacat gaccatcaaa accgaactcc    1140
ccctgggcgc acgcggaag atgaagccac tgctaccacg ggtcagctca tacctggtac    1200
ctatccagtt cccggtgaac cagtcactgg tgttgcagcc ctcggtgaag gtgccattgc    1260
ccctggcggc ttccctcatg agctcagagc ttgcccgcca tagcaagcga gtccgcattg    1320
cccccaaggt gctgctagct gaggagggga tagctcctct ttcttctgca ggaccaggga    1380
aagaggagaa actcctgttt ggagaagggt ttctcctttt gcttccagtt cagactatca    1440
aggaggaaga aatccagcct ggggaggaaa tgccacactt agcgagaccc atcaaagtgg    1500
agagccctcc cttggaagag tggccctccc cggccccatc tttcaaagag gaatcatctc    1560
actcctggga ggattcgtcc caatctccca ccccaagacc caagagtcc tacagtgggc    1620
```

-continued

```
ttaggtcccc aacccggtgt gtctcggaaa tgcttgtgat tcaacacagg gagaggaggg    1680
agaggagccg gtctcggagg aaacagcatc tactgcctcc ctgtgtggat gagccggagc    1740
tgctcttctc agaggggccc agtacttccc gctgggccgc agagctcccg ttcccagcag    1800
actcctctga ccctgcctcc cagctcagct actcccagga agtgggagga cctttttaaga   1860 cacccattaa ggaaacgctg cccatctcct ccaccccgag caaatctgtc ctccccagaa    1920
cccctgaatc ctggaggctc acgcccccag ccaaagtagg gggactggat ttcagcccag    1980
tacaaacctc ccagggtgcc tctgacccct tgcctgaccc cctggggctg atggatctca    2040
gcaccactcc cttgcaaagt gctcccccc ttgaatcacc gcaaaggctc ctcagttcag     2100
aacccttaga cctcatctcc gtccccttg gcaactcttc tccctcagat atagacgtcc     2160
ccaagccagg ctccccggag ccacaggttt ctggccttgc agccaatcgt tctctgacag    2220
aaggcctggt cctggacaca atgaatgaca gcctcagcaa gatcctgctg gacatcagct    2280
ttcctggcct ggacgaggac ccactgggcc ctgacaacat caactggtcc cagtttattc    2340
ctgagctaca gtagagccct gcccttgccc ctgtgctcaa gctgtccacc atcccgggca    2400
ctccaaggct cagtgcaccc caagcctctg agtgaggaca gcaggcaggg actgttctgc    2460
tcctcatagc tccctgctgc ctgattatgc aaaagtagca gtcacaccct agccactgct    2520
gggaccttgt gttccccaag agtatctgat tcctctgctg tccctgccag gagctgaagg    2580
gtgggaacaa caaaggcaat ggtgaaaaga gattaggaac cccccagcct gtttccattc    2640
tctgcccagc agtctcttac cttccctgat ctttgcaggg tggtccgtgt aaatagtata    2700
aattctccaa attatcctct aattataaat gtaagcttat ttccttagat cattatccag    2760
agactgccag aaggtgggta ggatgacctg gggtttcaat tgacttctgt tccttgcttt    2820
tagttttgat agaagggaag acctgcagtg cacggtttct tccaggctga ggtacctgga    2880
tcttgggttc ttcactgcag ggacccagac aagtggatct gcttgccaga gtccttttg     2940 cccctccctg ccacctcccc gtgtttccaa gtcagctttc ctgcaagaag aaatcctggt    3000
taaaaaagtc ttttgtattg ggtcaggagt tgaatttggg gtgggaggat ggatgcaact    3060
gaagcagagt gtgggtgccc agatgtgcgc tattagatgt ttctctgata atgtcccaa     3120 tcataccagg gagactggca ttgacgagaa ctcaggtgga ggcttgagaa ggccgaaagg    3180
gcccctgacc tgcctggctt ccttagcttg cccctcagct ttgcaaagag ccaccctagg    3240
ccccagctga ccgcatgggt gtgagccagc ttgagaacac taactactca ataaaagcga    3300
aggtggacaa aaaaaaaaaa aaaaaa                                         3326
```